(12) United States Patent
Koyejo et al.

(10) Patent No.: US 12,424,328 B2
(45) Date of Patent: Sep. 23, 2025

(54) COMORBIDITY PREDICTION FROM RADIOLOGY IMAGES

(71) Applicant: The Board of Trustees of the University of Illinois, Urbana, IL (US)

(72) Inventors: Oluwasanmi Koyejo, Urbana, IL (US); Andrew Chen, Urbana, IL (US); Patrick Cole, Urbana, IL (US); Nasir Siddiqui, Hinsdale, IL (US); Ayis Pyrros, Hinsdale, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 421 days.

(21) Appl. No.: 17/861,347

(22) Filed: Jul. 11, 2022

(65) Prior Publication Data

US 2023/0016569 A1 Jan. 19, 2023

Related U.S. Application Data

(60) Provisional application No. 63/220,315, filed on Jul. 9, 2021.

(51) Int. Cl.
*G16H 50/30* (2018.01)
*G06T 7/00* (2017.01)
(Continued)

(52) U.S. Cl.
CPC ........... *G16H 50/30* (2018.01); *G06T 7/0012* (2013.01); *G16H 30/40* (2018.01); *G16H 50/20* (2018.01);
(Continued)

(58) Field of Classification Search
CPC . G06T 2207/20084; G06T 2207/20081; G06T 7/0012; G06T 2207/10116;
(Continued)

(56) References Cited

U.S. PATENT DOCUMENTS 8,504,392 B2   8/2013   Saria
10,269,114 B2  4/2019   Reicher
(Continued)

OTHER PUBLICATIONS

Chakravarty, Arunava, et al. "Learning decision ensemble using a graph neural network for comorbidity aware chest radiograph screening." 2020 42nd Annual International Conference of the IEEE Engineering in Medicine & Biology Society (EMBC). IEEE, 2020. (Year: 2020).*

(Continued)

*Primary Examiner* — Gandhi Thirugnanam
*Assistant Examiner* — Connor L Hansen
(74) *Attorney, Agent, or Firm* — McDonnell Boehnen Hulbert & Berghoff LLP

(57) ABSTRACT

Methods are provided to predict, based on chest radiographs, whether a patient suffers from any comorbidities in one or more high-level comorbidity classes, e.g., high-level hierarchical condition categories. The chest radiograph is a low-cost, minimally-invasive source of visual information that is able to accurately predict whether a subject suffers from diabetes with chronic complications, morbid obesity, congestive heart failure, specified heart arrhythmias, vascular disease, or chronic obstructive pulmonary disease, among other high-level comorbidity classes. The predictive methods provided herein are also able to accurately predict overall measures of health-related complications, including the risk adjustment factor. These predictive methods can be used to focus review of medical records, improving the detection of disease. Outputs generated by these methods can also be used to predict the severity of disease and/or the extent of care provided to subjects with COVID-19 or related diseases.

20 Claims, 5 Drawing Sheets

(51) Int. Cl.
   *G16H 30/40* (2018.01)
   *G16H 50/20* (2018.01)
(52) U.S. Cl.
   CPC .............. *G06T 2207/20081* (2013.01); *G06T 2207/20084* (2013.01)
(58) Field of Classification Search
   CPC .......... G06T 2207/30061; G06V 10/82; G06V 10/26; G06V 2201/031; A61B 5/7267; A61B 5/7264; A61B 6/5217; A61B 8/5223; A61B 5/7275; G06F 18/2431; G06F 18/24; G16H 50/20; G16H 50/30; G16H 70/60; G16H 50/00; G16H 30/00
   See application file for complete search history.

(56) References Cited

U.S. PATENT DOCUMENTS

| | | | |
|---|---|---|---|
| 2004/0172297 A1 | 9/2004 | Rao | |
| 2010/0094649 A1 | 4/2010 | White | |
| 2015/0100344 A1* | 4/2015 | Chen | G16H 50/30 705/2 |
| 2020/0160301 A1 | 5/2020 | Lyman | |
| 2020/0265276 A1* | 8/2020 | Xu | G06V 10/454 |
| 2020/0357118 A1* | 11/2020 | Yao | G06N 3/045 |
| 2021/0042916 A1* | 2/2021 | Zhang | A61B 6/50 |
| 2024/0145093 A1* | 5/2024 | Rodriguez | G16H 80/00 |

OTHER PUBLICATIONS

Gong, Kuang, et al. "A multi-center study of COVID-19 patient prognosis using deep learning-based CT image analysis and electronic health records." European journal of radiology 139 (2021): 109583. (Year: 2021).*
Gude-Sampedro, Francisco, et al. "Development and validation of a prognostic model based on comorbidities to predict COVID-19 severity: a population-based study." International journal of epidemiology 50.1 (2021): 64-74. (Year: 2021).*
Bang, TJ, et al., American College of Radiology. ACR Appropriateness Criteria: Routine Chest Radiography, 2023. https://acsearch.acr.org/docs/69451/Narrative/.
Bretz, F., Maurer, W., Brannath, W., Posch, M., A graphical approach to sequentially rejective multiple test procedures, Stat Med. 2009; 28: 586-604.
Gallino A, Aboyans V, Diehm C, et al. Non-coronary atherosclerosis. Eur Heart J May 2014;35(17):1112-1119.
Henkel, RJ, Maryland, PA. The risks and rewards of value-based reimbursement. Front Health Serv Manage 2015;32(2):3-16.
Joseph NP, Reid NJ, Som A, et al. Racial and ethnic disparities in disease severity on admission chest radiographs among patients admitted with confirmed coronavirus disease 2019: a retrospective cohort study. Radiology 2020;297(3):E303-E312.
Kerr IH. The preoperative chest X-ray. Br J Anaesth. 1974;46(8):558-563.
Khanna, K., et al., Who Are You? Bayesian Prediction of Racial Category Using Surname and Geolocation website. Updated May 17, 2021. Accessed Jun. 30, 2021. https://github.com/kosukeimai/wru.
Ortega P, Martinez G, Diamond L. Language and health equity during COVID-19: lessons and opportunities. J Health Care Poor Underserved 2020;31(4):1530-1535.
Robert Graham Center. Social Deprivation Index (SDI) website. Accessed Jun. 30, 2021. https://www.graham-center.org/rgc/maps-data-tools/sdi/social-deprivation-index.html.
Schachterle, S.E., Hurley, S., Liu, Q. et al. An Implementation and Visualization of the Tree-Based Scan Statistic for Safety Event Monitoring in Longitudinal Electronic Health Data. Drug Saf 42, 727-741 (2019). https://doi.org/10.1007/s40264-018-00784-0.
Schut RA. Racial disparities in provider-patient communication of incidental medical findings. Soc Sci Med. Apr. 6, 2021;277:113901.
Straw I. The automation of bias in medical Artificial Intelligence (AI): Decoding the past to create a better future. Artif Intell Med Nov. 2020;110:101965.
Ward JB, Gartner DR, Keyes KM, Fliss MD, McClure ES, Robinson WR. How do we assess a racial disparity in health? Distribution, interaction, and interpretation in epidemiological studies. Ann Epidemiol Jan. 2019;29:1-7.
Webb Hooper M, Nápoles AM, Pérez-Stable EJ. COVID-19 and racial/ethnic disparities. JAMA 2020;323(24):2466-2467. doi:10.1001/jama.2020.8598.
2019 model software/icd-10 mappings. Centers for Medicare and Medicaid Services Web site. https://www.cms.gov/Medicare/Health-Plans/MedicareAdvtgSpecRateStats/Risk-Adjustors-Items/RiskModel2019. Accessed Feb. 23, 2021.
Adar A, Onalan O, Keles H, Cakan F, Kokturk U. Relationship between aortic arch calcification, detected by chest x-ray, and renal resistive index in patients with hypertension. MPP. 2019;28(2):133-40.
Argyriou A, Evgeniou T, Pontil M. Convex multi-task feature learning. Mach Learn. Dec. 2008;73(3):243-72.
Brady AP, Bello JA, Derchi LE, et al. Radiology in the era of value-based healthcare: A multi-society expert statement from the ACR, CAR, ESR, IS3R, RANZCR, and RSNA. Radiology 2021;298(3):486-491.
Captum • model interpretability for pytorch. https://captum.ai/ Accessed Feb. 23, 2021.
Caruana R. Multitask learning: a knowledge-based source of inductive bias. In: Proceedings of the Tenth International Conference on International Conference on Machine Learning. Amherst, MA, USA: Morgan Kaufmann Publishers Inc.; 1993. p. 41-48. (ICML'93).
Chen T, Guestrin C. Xgboost: a scalable tree boosting system. In: Proceedings of the 22nd ACM SIGKDD International Conference on Knowledge Discovery and Data Mining [Internet]. San Francisco, California, USA: Association for Computing Machinery; 2016 [cited Nov. 17, 2020]. p. 785-794. (KDD '16). Available from: https://doi.org/10.1145/2939672.2939785.
Cohen J, Chester: A Web Delivered Locally Computed Chest X-Ray Disease Prediction System, Feb. 2, 2020, arXiv:1901.11210v3, https://doi.org/10.48550/arXiv.1901.11210.
Collobert R, Weston J. A unified architecture for natural language processing: deep neural networks with multitask learning. In: Proceedings of the 25th international conference on Machine learning—ICML '08 [Internet]. Helsinki, Finland: ACM Press; 2008 [cited Nov. 17, 2020]. p. 160-7. Available from: http://portal.acm.org/citation.cfm?doid=1390156.1390177.
De Groot V, Beckerman H, Lankhorst GJ, Bouter LM. How to measure comorbidity. a critical review of available methods. J Clin Epidemiol. Mar. 2003;56(3):221-9.
DeLong Elisabeth R., David M. DeLong and Daniel L. Clarke-Pearson "Comparing the areas under two or more correlated receiver operating characteristic curves: a nonparametric approach". Biometrics 1988; 44, 837-845.
Dodge S, Karam L. Understanding how image quality affects deep neural networks. Arxiv 1604.04004 [preprint] http://arxiv.org/abs/1604.04004Posted Apr. 21, 2016. Accessed Feb. 23, 2021.24.
Gupta RK, Marks M, Samuels TH, et al. Systematic evaluation and external validation of 22 prognostic models among hospitalised adults with COVID-19: An observational cohort study. European Respiratory Journal 2020; 56.
Harutyunyan H, Khachatrian H, Kale DC, Ver Steeg G, Galstyan A. Multitask learning and benchmarking with clinical time series data. Scientific Data. Jun. 17, 2019;6(1):96.
Holm, S. "A simple sequentially rejective multiple test procedure". Scandinavian Journal of Statistics 1979; 6 (2): 65-70.
Hosmer. Applied logistic regression, 3rd edition. Hoboken, New Jersey: Wiley; 2013.
Huang C, Wang Y, Li X, Ren L, Zhao J, Hu Y, et al. Clinical features of patients infected with 2019 novel coronavirus in Wuhan, China. The Lancet. Feb. 15, 2020;395(10223):497-506.
Irvin, et al., CheXpert: A Large Chest Radiograph Dataset with Uncertainty Labels and Expert Comparison, Jan. 21, 2019, arXiv:1901.07031v1, https://doi.org/10.48550/arXiv.1901.07031.

(56) References Cited

OTHER PUBLICATIONS

Juhnke C, Bethge S, Mühlbacher AC. A review on methods of risk adjustment and their use in integrated healthcare systems. Int J Integr Care [Internet]. [cited Nov. 17, 2020];16(4). Available from: https://www.ncbi.nlm.nih.gov/pmc/articles/PMC5354219/.

Karargyris A, Kashyap S, Wu JT, Sharma A, Moradi M, Syeda-Mahmood T. Age prediction using a large chest X-ray dataset. arXiv: 190306542 [cs] [Internet]. Mar. 8, 2019 [cited Nov. 17, 2020]; Available from: http://arxiv.org/abs/1903.06542.

Ke G, Meng Q, Finley T, Wang T, Chen W, Ma W, et al. Lightgbm: a highly efficient gradient boosting decision tree. Advances in Neural Information Processing Systems. 2017;30:3146-54.

Kim HW, Capaccione KM, Li G, Luk L, Widemon RS, Rahman O, et al. The role of initial chest X-ray in triaging patients with suspected COVID-19 during the pandemic. Emerg Radiol. Jun. 22, 2020;1-5.

Kim YS, Park HY, Yun K-H, Park H, Cheong JS, Ha YS. Association of aortic knob calcification with intracranial stenosis in ischemic stroke patients. J Stroke. May 2013;15(2):122-5.

King Jr JT, Yoon JS, Rentsch CT, et al. Development and validation of a 30-day mortality index based on pre-existing medical administrative data from 13,323 COVID-19 patients: The Veterans Health Administration COVID-19 (Vaco) Index. PLoS One 2020;15(11):e0241825.

Kingma DP, Ba J. Adam: a method for stochastic optimization. arXiv: 14126980 [cs] [Internet]. Jan. 29, 2017 [cited Nov. 17, 2020]; Available from: http://arxiv.org/abs/1412.6980.

Liaw A, Wiener M. Classification and regression by randomForest. R news. 2002;2(3):18-22.

Liu R, Lehman J, Molino P, Such FP, Frank E, Sergeev A, et al. An intriguing failing of convolutional neural networks and the coordconv solution. arXiv:180703247 [cs, stat] [Internet]. Dec. 3, 2018 [cited Nov. 17, 2020]; Available from: http://arxiv.org/abs/1807.03247.

Lu MT, Ivanov A, Mayrhofer T, Hosny A, Aerts HJWL, Hoffmann U. Deep learning to assess longterm mortality from chest radiographs. JAMA Netw Open. Jul. 19, 2019;2(7):e197416.

Ma X, Ng M, Xu S, Xu Z, Qiu H, Liu Y, et al. Development and validation of prognosis model of mortality risk in patients with COVID-19. Epidemiology & Infection [Internet]. 2020 ed [cited Nov. 17, 2020];148. Available from: https://www.cambridge.org/core/journals/epidemiology-andinfection/article/development-and-validation-of-prognosis-model-of-mortality-risk-in-patients-withcovid19/9A3B09B53AF543DDF0BC8F1348EFF07C.

Mamlin BW, Heinze DT, McDonald CJ. Automated extraction and normalization of findings from cancer-related free-text radiology reports. AMIA Annu Symp Proc. 2003;2003:420-4. PMID: 14728207; PMCID: PMC1479955.

Mandal AK, Tagomori GK, Felix RV, Howell SC. Value-based contracting innovated Medicare advantage healthcare delivery and improved survival. Am J Manag Care 2017;23(2):e41-e49. PMID: 28245661.

Mosley DG, Peterson E, Martin DC. Do hierarchical condition category model scores predict hospitalization risk in newly enrolled Medicare advantage participants as well as probability of repeated admission scores? J Am Geriatr Soc 2009;57(12):2306-2310.

Pan F, Ye T, Sun P, et al. Time course of lung changes at chest CT during recovery from coronavirus disease 2019 (COVID-19). Radiology 2020;295(3):715-721.

Prokhorenkova L, Gusev G, Vorobev A, Dorogush AV, Gulin A. CatBoost: unbiased boosting with categorical features. In: Proceedings of the 32nd International Conference on Neural Information Processing Systems. Montréal, Canada: Curran Associates Inc.; 2018. p. 6639-6649. (NIPS'18).

Rajpurkar P, Irvin J, Ball RL, Zhu K, Yang B, et al. (2018) Deep learning for chest radiograph diagnosis: A retrospective comparison of the CheXNeXt algorithm to practicing radiologists. PLOS Medicine 15(11): e1002686. https://doi.org/10.1371/journal.pmed.1002686.

Richardson S, Hirsch JS, Narasimhan M, Crawford JM, McGinn T, Davidson KW, et al. Presenting characteristics, comorbidities, and outcomes among 5700 patients hospitalized with covid-19 in the new york city area. JAMA. May 26, 2020;323(20):2052.

Robinson JC. Medicare Advantage reimbursement to physicians. JAMA Intern Med 2017;177(9):1295-1296. doi: 10.1001/jamainternmed.2017.2689. PMID: 28692717.

Rubin GD. Costing in radiology and health care: Rationale, relativity, rudiments, and realities. Radiology 2017;282(2):333-347.

Ruder, S., An Overview of Multi-Task Learning in Deep Neural Networks. CoRR 1706.05098, 2017, http://arxiv.org/abs/1706.05098.

Safavian SR, Landgrebe D. A survey of decision tree classifier methodology. IEEE Transactions on Systems, Man, and Cybernetics. May 1991;21(3):660-74.

Schalekamp S, Huisman M, van Dijk RA, Boomsma M f., Freire Jorge P j., de Boer W s, et al. Modelbased prediction of critical illness in hospitalized patients with covid-19. Radiology. Aug. 13, 2020;202723.

Selvaraju RR, Cogswell M, Das A, Vedantam R, Parikh D, Batra D. Grad-cam: visual explanations from deep networks via gradient-based localization. Int J Comput Vis. Feb. 2020;128(2):336-59.

Tallam H, Elton DC, Lee S, Wakim P, Pickhardt PJ, Summers RM. Fully Automated Abdominal CT Biomarkers for Type 2 Diabetes Using Deep Learning. Radiology. Apr. 5, 2022:211914. doi: 10.1148/radiol.211914. Epub ahead of print. PMID: 35380492.

Toussie D, Voutsinas N, Finkelstein M, Cedillo MA, Manna S, Maron SZ, et al. Clinical and chest radiography features determine patient outcomes in young and middle-aged adults with covid-19. Radiology. Oct. 2020;297(1):E197-206.

Wang L, Wong A. Covid-net: a tailored deep convolutional neural network design for detection of covid-19 cases from chest x-ray images. arXiv:200309871 [cs, eess] [Internet]. May 11, 2020 [cited Nov. 17, 2020]; Available from: http://arxiv.org/abs/2003.09871.

Williamson EJ, Walker AJ, Bhaskaran K, et al. Factors associated with COVID-19-related death using OpenSAFELY. Nature 2020;584(7821):430-436.

Wynants L, Calster BV, Collins GS, Riley RD, Heinze G, Schuit E, et al. Prediction models for diagnosis and prognosis of covid-19: systematic review and critical appraisal. BMJ [Internet]. Apr. 7, 2020 [cited Nov. 17, 2020];369. Available from: https://www.bmj.com/content/369/bmj.m1328.

Yang J, Zheng Y, Gou X, Pu K, Chen Z, Guo Q, et al. Prevalence of comorbidities and its effects in patients infected with SARS-CoV-2: a systematic review and meta-analysis. Int J Infect Dis. May 2020;94:91-5.

Yu C, Lei Q, Li W, Wang X, Liu W, Fan X, et al. Clinical characteristics, associated factors, and predicting covid-19 mortality risk: a retrospective study in wuhan, china. American Journal of Preventive Medicine. Aug. 1, 2020;59(2):168-75.

Zhang Z. Multivariable fractional polynomial method for regression model. Ann Transl Med. May 2016;4(9):174. doi: 10.21037/atm.2016.05.01. PMID: 27275487; PMCID: PMC4876277.

* cited by examiner

COMORBIDITY PREDICTION FROM RADIOLOGY IMAGES

CROSS-REFERENCE TO RELATED APPLICATION

This application claims priority to U.S. Provisional Patent Application No. 63/220,315, filed Jul. 9, 2021, the contents of which are incorporated by reference.

BACKGROUND

In many applications, a machine learning model (e.g., an artificial neural network, a support vector machine, a regression tree) can be trained to classify an input (e.g., determine whether an input image contain a face or other feature) or to generate some other output that is indicative of a quality of the input (e.g., a likelihood that the input belong to a particular class, a degree to which the input corresponds to training inputs having a particular class). This can include applying a large number of training images, having associated therewith "ground truth" values for the contents of the images, to the machine learning model and then updating the model based on whether it correctly or incorrectly predicted the "ground truth" value(s) associated therewith.

SUMMARY

In a first aspect, a computer-implemented method is provided that includes: (i) receiving a target radiographic image of a chest of a subject, wherein an artificial neural network (ANN) has a set of inputs and a set of outputs, wherein the ANN has been trained by a training set including a plurality of radiographic images containing features that are mapped to the set of inputs and associated with labeled values mapped to the set of outputs, wherein a subset of the radiographic images contain instances of the features that are indicative of at least one comorbidity within a particular comorbidity class and are associated with instances of the labeled values that represent the particular comorbidity class; and (ii) applying the ANN to the target radiographic image to generate a set of target outputs for the target radiographic image, wherein output values of the set of target outputs indicate that the subject has at least one comorbidity in the particular comorbidity class.

In a second aspect, a non-transitory computer readable medium is provided having stored therein instructions executable by a computing device to cause the computing device to perform the method of the first aspect.

In a third aspect, a computing system is provided that includes: (i) a controller comprising one or more processors; and (ii) a non-transitory computer readable medium having stored therein instructions executable by the controller device to cause the one or more processors to perform the method of the first aspect.

The foregoing summary is illustrative only and is not intended to be in any way limiting. In addition to the illustrative aspects, embodiments, and features described above, further aspects, embodiments, and features will become apparent by reference to the figures and the following detailed description and the accompanying drawings.

DETAILED DESCRIPTION

Figure 1:
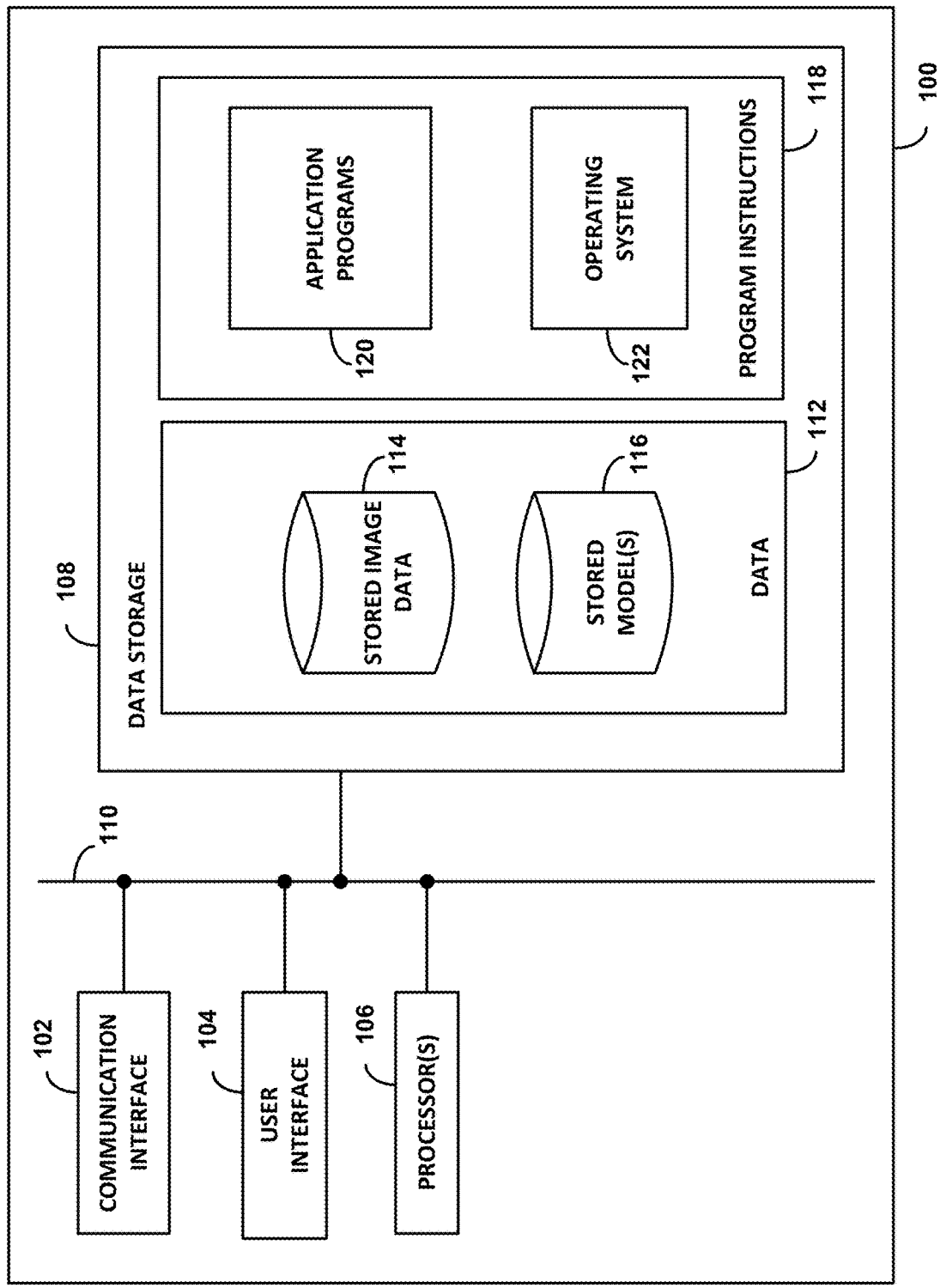
FIG. 1 illustrates aspects of an example system.

The following detailed description describes various features and functions of the disclosed systems and methods with reference to the accompanying figures. The illustrative system and method embodiments described herein are not meant to be limiting. It may be readily understood that certain aspects of the disclosed systems and methods can be arranged and combined in a wide variety of different configurations, all of which are contemplated herein.

I. OVERVIEW

It is beneficial in a healthcare setting to accurately diagnose a patient's underlying disease state in order to provide the correct care and protect the patient's health. Accordingly, it is advantageous for a healthcare system to be certain that it is accurately detecting and diagnosing all of a patient's conditions, so as not to provide inadequate or inappropriate care. It is also beneficial to track such accurate diagnoses over time, in order to monitor and/or adjust the course of a treatment. However, accurately diagnosing a patient, or verifying the accuracy of an existing diagnosis, can be expensive tasks, as they may require costly testing and/or clinician time to generate or confirm.

Embodiments described herein provide improved methods for predicting and applying high-level comorbidity class diagnoses (e.g., predicting that a patient has at least one comorbidity with a specified high-level class containing a range of related comorbidities) and other valuable diagnostic and treatment information for a patient based on chest radiographs (e.g., X-rays) or other available diagnostic medical imagery (e.g., radiographs of other body parts with or without the presence of contrast agents, MRI images, PET images). The chest radiograph is a low-cost diagnostic that is often already present in a patient's medical record as part of common past diagnostic efforts. Accordingly, the methods herein could be applied to diagnose, to track the disease progression of, and/or to audit or update the diagnosis of, past patients, e.g., patients whose chest radiographs are stored in a medical records database. The embodiments described herein are able to use the chest radiograph to predict a variety of high-level diagnostic information, including ICD10 hierarchical condition categories and risk adjustment factors that are directly determined for purposes of medical procedures.

This is an unexpected improvement on previous work, which was only capable of predicting specific discrete signs of particular diseases or syndromes. In contrast, the improvements described herein are capable of predicting high-level classes of diseases, syndromes, or other comorbidities and overall medical risk exhibited by a patient, including specified classes of comorbidities relevant to medical procedures. The comorbidity classes that the embodiments herein are capable of predicting from chest radiographs include diabetes with chronic complications (e.g., ICD10 hierarchical condition category HCC18), morbid obesity (e.g., HCC22), congestive heart failure (e.g., HCC85), specified heart arrhythmias (e.g., HCC96), vascular disease (e.g., HCC108), and chronic obstructive pulmonary disease (e.g., HCC111). The embodiments herein are also capable of accurately estimating the risk adjustment factor (RAF) for a patient based on the chest radiograph.

Another benefit of the present embodiments is that historical chest radiographs, with associated high-level comorbidity class, RAF, gender, age, and other labels, are easily and cost-effectively accessible. The predictive models described herein can thus be trained at low cost with large amounts of high-quality historical data. Once trained, such a model could be used to update or otherwise improve the training set, by applying the trained model to the training data in order to determine whether any of the labels for the training data do not match the model predictions. Those non-conforming records in the training data could then be audited (e.g., by a doctor or other healthcare professional) and, if necessary, updated. These updated records could be used to update statistical analyses of disease and/or of the operational efficacy of a healthcare system or of a particular medical intervention, or to modify ongoing or future treatment of a patient.

A trained model could then be used to generate high-level comorbidity class predictions (e.g., HCC code predictions), RAF predictions, or other diagnostic predictions based on new chest radiographs (e.g., chest radiographs taken of new patients, chest radiographs taken to track the progression of a disease state and/or treatment) or stored historical chest radiographs (e.g., to audit or update past records, to adjust treatment of a patient based on comorbidities detected in their historical chest radiograph(s)). These predictions could be used to plan treatment, to plan the performance of additional diagnostic tests, to plan future healthcare needs, to identify patients to recruit for a pharmaceutical or other treatment study, or to provide some other benefit.

The predictive models described herein can include artificial neural networks (ANNs) or other predictive models. In some examples, the model include one or more 'common' layers that receive the input chest radiograph and that provide a set of outputs to a number of output heads, each output head corresponding to a respective different output (e.g., RAF or other overall numerical measure of medical risk, HCC code or other high-level comorbidity class). The use of such a structure allows the labels for multiple different comorbidity classes or other outputs (e.g., RAF) to inform the training of the common layers, leading to improved overall accuracy. The use of specified numbers of predicted outputs and/or sets of predicted outputs resulted in improved predictive accuracy, as fewer outputs (e.g., as few as one output) provided too little information to effectively train a full ANN, while attempting to predict too many outputs and/or incorrect outputs also resulted in degraded accuracy relative to the number and set of predicted outputs described herein. One set of predicted outputs that resulted in high-accuracy predictions included gender, age, RAF score, HCC18 status, HCC22 status, HCC85 status, HCC96 status, HCC108 status, and HCC111 status.

As noted above, these trained models can be used to determine a course of treatment. In a particular example, the output(s) of such a model could be used to determine whether to perform additional diagnostic tests. Such tests could be expensive, difficult to perform, unpleasant or potentially dangerous to the patient, or otherwise undesirable to perform unless needed. One or more of the outputs of the trained model could be used to predict a likelihood that a patient has a particular condition or disease. If the likelihood is high enough (e.g., greater than a first threshold), additional testing could be performed to confirm and/or quantify the diagnosis. Additionally or alternatively, the additional testing could be performed only if the likelihood has an intermediate value (e.g., greater than the first threshold, but less than a second threshold). This could be done in cases where a high likelihood output from the model is very accurate (e.g., very low chance of false positive), negating the benefit of performing follow-up verification via additional testing in cases where the model has predicted a high likelihood.

These trained models can also be used to indicate, on a chest radiograph, which portions of the chest radiograph are particularly relevant to the predicted diagnosis (e.g., areas that contributed 'more' to a particular predicted output). This could be done to indicate the 'location' of tissue that is diseased or to otherwise provide a clinician with potential context as to 'why' a particular diagnosis or other output was generated. This can be done by repeatedly applying modified versions of an input chest radiograph to the model, with each modified version differing with respect to which portion of the input chest radiograph is blanked out. The numerical value of an output of interest could then be plotted as a function of which area of the input radiograph was 'blanked', thus generating an image of the areas of the unmodified input radiograph that are most 'influential' on the output of interest.

The outputs of such a model could, themselves, be used to predict further outputs. For example, the probability or morbidity, mortality, or certain other outcomes related to a specified disease, syndrome, or other condition (e.g., COVID-19). The outputs could be used to predict the probability of death or other specified outcomes related to a specified condition, to predict the likelihood that a patient will be hospitalized for more than a specified duration (e.g., two days) or will require some other intervention, or to predict some other outcome or status. Such a prediction could include generating a weighted sum of the outputs of the model (e.g., a number of the predicted high-level comorbidity classes that were predicted as present for a patient, or a sum of the raw outputs of the model related thereto) and comparing that sum to a threshold. In another example, the outputs could be applied to a generalized linear model (GLM) to predict the outcome related to the specified condition. Other potential predictive outputs, either as raw outputs of the base model or derived outputs determined therefrom (e.g., via an additional model trained on the base model's outputs) could include eventual need for dialysis, claim fraud and/or coding error in a patient's health history (when also provided with data representing that health history and/or billing history), patient-specific drug efficacy (e.g., to select the 'most effective' drug for a patient from a set of possible drugs to treat a condition), risk and/or presence of emphysema, chronic obstructive pulmonary disease, or type 2 diabetes and/or the need for a patient to receive additional diagnostic screening related thereto (e.g., to provide clinical decision support related to the decision to apply additional diagnostics to a patient), body mass index (BMI), hemoglobin A1C, glomerular flow resistance, C-reactive protein levels, or other predictive outputs.

Using the model outputs in such a way allows the high-accuracy prediction of generally-relevant high-level classes of comorbidities (e.g., chronic diabetes, morbid obesity, etc.) to be applied to novel, rare, or other specified diseases where there may not be sufficient data (e.g., sufficient chest radiographs) to train a high-quality predictive model. Instead, data limited to the outputs of the existing model (which was trained on a large corpus of high-quality historical data) can be collected for patients exhibiting the specified condition and used to determine the significantly fewer parameters involved in a GLM or other predictor (e.g., the weights and/or threshold value of the weighted sum predictor described above). In some examples, the outputs generated by the pre-trained model could be augmented with additional outputs specific to the specified condition. For example, a chest radiograph could be applied to the model described above to generate RAF, HCC status, or other outputs. The chest radiograph could also be applied to an additional ANN or other model trained to determine severity, degree, or extent of lung opacity represented in the radiograph. The outputs of both models could then be used (e.g., applied to a GLM, summed and compared to a threshold) to predict whether the patient is likely to experience a specified outcome or to receive a specified type or degree of treatment.

The methods described herein have a high demonstrated utility in predicting a variety of high-level classes of comorbidities or other useful diagnostic information (e.g., RAF, diagnosis of specific conditions like diabetes). For example, the methods described herein were able to predict, based on chest radiographs, dementia with an AUC ("area under the curve") of 0.86 and renal failure with dialysis with an AUC of 0.81.

Note that the models described herein can be trained to generate the outputs described herein based on chest radiographs or additional or alternative imaging inputs. For example, such a model could be trained to receive as input two chest radiographs, representing perpendicular views of the same patient's chest. In another example, MM, X-ray angiograms, or other medical diagnostic imagery could additionally or alternatively be applied as inputs to such a model These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

II. EXAMPLE SYSTEMS

FIG. 1 illustrates an example system 100 that may be used to implement the methods described herein. By way of example and without limitation, system 100 may be or include a computer (such as a desktop, notebook, tablet, or handheld computer, a server), elements of a cloud computing system, or some other type of device or system. It should be understood that elements of system 100 may represent a physical instrument and/or computing device such as a server, a particular physical hardware platform on which applications operate in software, or other combinations of hardware and software that are configured to carry out functions as described herein.

As shown in FIG. 1, system 100 may include a communication interface 102, a user interface 104, one or more processor(s) 106, and data storage 108, all of which may be communicatively linked together by a system bus, network, or other connection mechanism 110.

Communication interface 102 may function to allow system 100 to communicate, using analog or digital modulation of electric, magnetic, electromagnetic, optical, or other signals, with other devices (e.g., with digital X-ray imagers or other imaging systems that generate relevant image data for patients, with databases that contain sets of training inputs or related data, e.g., chest x-rays or other radiographic images of the chest or other anatomy of patients, ICD10 codes or other diagnostic classifications for such patients), access networks, and/or transport networks. Thus, communication interface 102 may facilitate circuit-switched and/or packet-switched communication, such as plain old telephone service (POTS) communication and/or Internet protocol (IP) or other packetized communication. For instance, communication interface 102 may include a chipset and antenna arranged for wireless communication with a radio access network or an access point. Also, communication interface 102 may take the form of or include a wireline interface, such as an Ethernet, Universal Serial Bus (USB), or High-Definition Multimedia Interface (HDMI) port. Communication interface 102 may also take the form of or include a wireless interface, such as a Wifi, BLUETOOTH®, global positioning system (GPS), or wide-area wireless interface (e.g., 3GPP Long-Term Evolution (LTE), or 3GPP 5G). However, other forms of physical layer interfaces and other types of standard or proprietary communication protocols may be used over communication interface 102. Furthermore, communication interface 102 may comprise multiple physical communication interfaces (e.g., a Wifi interface, a BLUETOOTH® interface, and a wide-area wireless interface).

In some embodiments, communication interface 102 may function to allow system 100 to communicate, with other devices, remote servers, access networks, and/or transport networks. For example, the communication interface 102 may function to communicate with one or more servers (e.g., servers of a cloud computer system that provide computational resources for a fee) to provide chest x-rays or other diagnostic images and to receive, in response, output values (e.g., predictions regarding a patient's corresponding to one or more ICD10 codes or other diagnostic information for a patient) or other types of data that can be applied as described herein. In another example, the communication interface 102 may function to communicate with one or more cellphones, tablets, or other computing devices.

User interface 104 may function to allow system 100 to interact with a user, for example to receive input from and/or to provide output to the user. Thus, user interface 104 may include input components such as a keypad, keyboard, touch-sensitive or presence-sensitive panel, computer mouse, trackball, joystick, microphone, and so on. User interface 104 may also include one or more output components such as a display screen which, for example, may be combined with a presence-sensitive panel. The display screen may be based on CRT, LCD, and/or LED technologies, or other technologies now known or later developed. User interface 104 may also be configured to generate audible output(s), via a speaker, speaker jack, audio output port, audio output device, earphones, and/or other similar devices.

Processor(s) 106 may comprise one or more general purpose processors—e.g., microprocessors—and/or one or more special purpose processors—e.g., digital signal processors (DSPs), graphics processing units (GPUs), floating point units (FPUs), network processors, tensor processing units (TPUs), or application-specific integrated circuits (ASICs). In some instances, special purpose processors may be capable of model execution (e.g., execution of artificial neural networks or other machine learning models), calibration and/or thresholding of model outputs, bucketizing of model outputs, determining calibrations or thresholds for model outputs, or other functions as described herein, among other applications or functions. Data storage 108 may include one or more volatile and/or non-volatile storage components, such as magnetic, optical, flash, or organic storage, and may be integrated in whole or in part with processor(s) 106. Data storage 108 may include removable and/or non-removable components.

Processor(s) 106 may be capable of executing program instructions 118 (e.g., compiled or non-compiled program logic and/or machine code) stored in data storage 108 to carry out the various functions described herein. Therefore, data storage 108 may include a non-transitory computer-readable medium, having stored thereon program instructions that, upon execution by system 100, cause system 100 to carry out any of the methods, processes, or functions disclosed in this specification and/or the accompanying drawings. The execution of program instructions 118 by processor(s) 106 may result in processor 106 using data 112.

By way of example, program instructions 118 may include an operating system 122 (e.g., an operating system kernel, device driver(s), and/or other modules) and one or more application programs 120 (e.g., functions for executing the methods described herein) installed on system 100. Data 112 may include stored image data 114 (e.g., radiographic images of chests of patients or other diagnostic images and ICD10 codes or other diagnostic information related thereto). Data 112 may also include stored models 116 (e.g., stored model parameters and other model-defining information) that can be executed as part of the methods described herein (e.g., to determine, from an input image, one or more model outputs that can then be used to diagnose a patient, to determine a treatment to provide to a patient, to determine whether to perform additional diagnostic tests on a patient, to monitor the progression of a disease or other condition of a patient, to indicate that a patient's health records and/or billing should be audited).

Application programs 120 may communicate with operating system 122 through one or more application programming interfaces (APIs). These APIs may facilitate, for instance, application programs 120 transmitting or receiving information via communication interface 102, receiving and/or displaying information on user interface 104, and so on.

Application programs 120 may take the form of "apps" that could be downloadable to system 100 through one or more online application stores or application markets (via, e.g., the communication interface 102). However, application programs can also be installed on system 100 in other ways, such as via a web browser or through a physical interface (e.g., a USB port) of the system 100.

III. EXAMPLE METHODS

Figure 2:
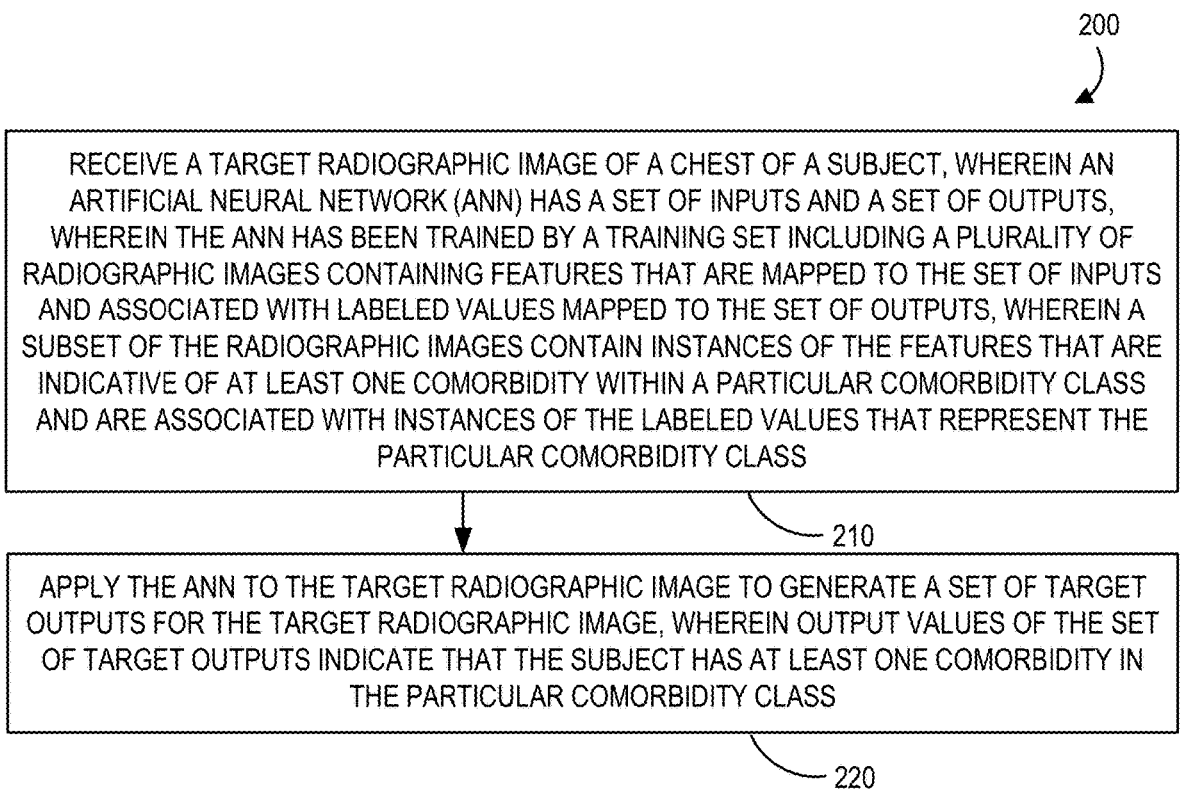
FIG. 2 illustrates a flowchart of an example method.

FIG. 2 depicts an example method 200. The method 200 includes receiving a target radiographic image of a chest of a subject, wherein an artificial neural network (ANN) has a set of inputs and a set of outputs, wherein the ANN has been trained by a training set including a plurality of radiographic images containing features that are mapped to the set of inputs and associated with labeled values mapped to the set of outputs, wherein a subset of the radiographic images contain instances of the features that are indicative of at least one comorbidity within a particular comorbidity class and are associated with instances of the labeled values that represent the particular comorbidity class (210). The method 200 additionally includes applying the ANN to the target radiographic image to generate a set of target outputs for the target radiographic image, wherein output values of the set of target outputs indicate that the subject has at least one comorbidity in the particular comorbidity class (220). The method 200 could include additional steps or features. The method 200 can additionally include (i) receiving a pre-determined set of outputs for the target radiographic image, wherein output values of the pre-determined set of outputs for the target radiographic image indicate that the subject does not have at least one comorbidity within the particular comorbidity class; (ii) determining that the pre-determined set of outputs for the target radiographic image differs from the set of target outputs generated by the ANN with respect to the subject having at least one comorbidity within the particular comorbidity class; and (iii) responsively providing an indication via a user interface that the pre-determined set of outputs for the target radiographic image differs from the set of target outputs generated by the ANN. In the method 200, the labeled values mapped to the set of outputs can include a numerical output that is indicative of an overall degree of medical risk, and the method 200 can additionally include: (i) receiving a pre-determined numerical indication of the overall degree of medical risk of the subject; (ii) determining that the pre-determined numerical indication of the overall degree of medical risk of the subject differs by more than a specified threshold amount from the output, of the set of target outputs generated by the ANN, that is indicative of the overall degree of medical risk of the subject; and (iii) responsively providing an indication via a user interface that the pre-determined numerical indication of the overall degree of medical risk of the subject differs from the output, of the set of target outputs generated by the ANN, that is indicative of the overall degree of medical risk of the subject.

It should be understood that arrangements described herein are for purposes of example only. As such, those skilled in the art will appreciate that other arrangements and other elements (e.g. machines, interfaces, operations, orders, and groupings of operations, etc.) can be used instead of or in addition to the illustrated elements or arrangements.

IV. DETECTION OF DIABETES FROM FRONTAL CHEST RADIOGRAPHY

Chest radiographs (CXRs) are one of the most frequently ordered radiological exams and can potentially be utilized as a biomarker. A multitask deep learning (DL) model as described above was used to detect diabetes from ambulatory frontal radiographs in a large clinical dataset.

The multitask DL model was trained and tested on 303,604 (55% female; mean age, 58) frontal CXRs from 2010 to 2021 at a single institution, using PyTorch and ResNet34, with 5-fold cross-validation. Patient age, BMI, HbA1c, diabetes, and select comorbidities (CHF, cardiac arrhythmias, morbid obesity, COPD, and vascular disease) from the electronic health record (EHR) were then validated on CXRs from ambulatory patients on out-of-fold predictions. Ground truth labels for diabetes were based on ICD10 codes and HbA1c$>=$6.5%. Days between diagnosis of diabetes and initial CXR were calculated. Patients with a diagnosis of diabetes predating the CXR were excluded, as well as patients with less than a year of follow-up. The discriminatory ability of the DL model was assessed using area under receiver operating characteristic curve (ROC AUC) compared with the ground truth labels and with other predictors (BMI, Social Deprivation Index). An optimal threshold was calculated using Youden's index from the DL predictor. CXR occlusion maps were generated.

A total of 104,473 CXRs in unique patients (mean age, 53; ±17 [SD]; 56% women) were evaluated in the final validation set, of whom 9,319 (8.9%) had a diagnosis of diabetes. The model's overall discriminatory ability for diabetes was an ROC AUC of 0.819 (95% CI: 0.815-0.823), versus ROC AUC of 0.542 (95% CI: 0.536-0.548) using social deprivation index (SDI) as a predictor, and AUC 0.686 (95% CI: 0.681-0.692) using BMI, with all curves demonstrating comparative p-values <0.001. The mean number of days from CXR to diabetes diagnosis was 1,009 (±953 [SD]). At an optimal threshold of 0.11 for the DL predictor, the sensitivity, specificity, negative predictive value, and positive predictive value was 79%, 69%, 97%, and 20%, respectively. Of the 37,265 patients above the threshold, 29,800 (79%) patients did not have a diagnosis of diabetes, and of those, 13,804 (46%) did not have a HbA1c value and 8,109 (27%) had a HbA1c between 5.7-6.4%.

Thus, chest radiography can be utilized to aid in detecting patients with diabetes and prediabetes using the methods described herein. The clinical relevance is that earlier detection of diabetes may allow for improved screening and intervention, potentially reducing the time to diagnosis and treatment.

V. PREDICTION OF MORTALITY AND COMORBIDITIES FROM CHEST RADIOGRAPHS IN COVID-19

A deep learning model as described herein was developed to predict comorbidities from frontal chest radiographs (CXRs) in patients with COVID-19 and the model's performance was compared with hierarchical condition category (HCC) mortality outcomes in COVID-19. The model was trained and tested on 14,121 ambulatory frontal CXRs from 2010 to 2019 at a single institution, modeling select comorbidities using the value-based Medicare Advantage HCC Risk Adjustment Model. Sex, age, HCC codes, and risk adjustment factor (RAF) score were used. The model was validated on frontal CXRs from 413 ambulatory patients with COVID-19 (internal cohort) and on initial frontal CXRs from 487 COVID-19 hospitalized patients (external cohort). The discriminatory ability of the model was assessed using receiver operating characteristic (ROC) curves compared to the HCC data from electronic health records, and predicted age and RAF score were compared using correlation coefficient and absolute mean error. The model predictions were used as covariables in logistic regression models to evaluate the prediction of mortality in the external cohort. Predicted comorbidities from frontal CXRs, including diabetes with chronic complications, obesity, congestive heart failure, arrhythmias, vascular disease, and chronic obstructive pulmonary disease, had a total area under ROC curve (AUC) of 0.85 (95% CI: 0.85-0.86). The ROC AUC of predicted mortality for the model was 0.84 (95% CI: 0.79-0.88) for the combined cohorts. This model using only frontal CXRs predicted select comorbidities and RAF score in both internal ambulatory and external hospitalized COVID-19 cohorts and was discriminatory of mortality, supporting its potential use in clinical decision making.

Managed care, also known as value-based care (VBC) in the US, emphasizes improved outcomes and decreased costs by managing chronic comorbidities and grouping (ICD10) diagnosis codes with reimbursements proportioned to disease burden. There is growing concern that these VBC models do not recognize radiology's central role. Radiologists are often unfamiliar with the complexity of VBC systems and their significance to clinical practice. Furthermore, radiologists frequently receive limited relevant clinical information on the radiology request; instead, clinical information is buried in the non-radiology electronic health record (EHR) data which is at best awkward and time-consuming to retrieve and at worst simply un-obtainable.

The risk adjustment factor (RAF) score, also called the Medicare risk adjustment, represents the amalgamation of the ICD10 hierarchical condition categories (HCCs) for a patient. The 2019 version 23 model includes 83 HCCs, comprising over 9,500 ICD10 codes, each having a numeric coefficient. There are additional coefficients for HCC interactions (disease interactions) and demographics composed of age and sex for patients over the age of 65 years. The RAF score directly correlates with disease burden, and likewise future healthcare costs, with the mean value calibrated to 1.0. A score of 1.1 indicates an approximately 10% higher reimbursement for a patient as the predicted costs are higher. The RAF score is calibrated yearly through updates to the Centers for Medicare and Medicaid Services (CMS) model coefficients and HCCs. In this work model version 23 from 2019 was used. The HCC codes were generated through encounters with healthcare providers and recorded in administrative data. As such, these data elements are often more reproducible and amenable to analysis than manual EHR review. These administrative data have been shown to predict mortality in patients with COVID-19.

The COVID-19 pandemic has strained healthcare systems worldwide, amplifying existing deficiencies. While most infected individuals experience mild or no symptoms, some become severely ill, require prolonged hospitalization, and succumb to the disease. Comorbidities such as diabetes, cardiovascular disease, and morbid obesity are associated with worse outcomes. Comorbidity data have been extracted from contemporaneously provided patient history, manual records, and/or EHRs. Such methods are imperfect, often incomplete, difficult to replicate across institutions, or not available for physician decision-making.

Multiple predictive clinical models of the course of COVID-19 infection have been developed utilizing demographic information, clinically obtained data regarding comorbidities, laboratory markers, and radiography. In these models, radiography has been incorporated by quantifying the geographic extent and degree of lung opacity. Using a convolutional neural network (CNN) to "link" HCCs and RAF scores to radiographs can convert the images into useful biomarkers of patients' chronic disease burden. Frontal chest radiographs (CXRs) have been used to directly predict or quantify patient comorbidities that contribute to outcomes.

The models and training methods described herein were used to apply VBC data and CXRs to train a deep learning (DL) model to predict select comorbidities and RAF scores; these predictions are able be used to model COVID-19 mortality.

Image Selection, Acquisition and Pre Processing

CXRs for the base training set were developed from 14,121 posteroanterior (PA) CXRs done from 2010 to 2019 at a large suburban multi-specialty practice, obtained conventionally with digital PA radiography. CXRs from the external validation set were portable anteroposterior (AP) radiographs, except for 30 conventionally obtained AP radiographs. All CXRs were extracted from a picture archiving and communication system (PACS) system utilizing a scripted method (SikuliX, 2.0.2) and saved as de-identified 8-bit grayscale portable network graphics (PNG) files for the training and internal validation sets and 24-bit Joint Photographic Experts Group (JPEG) files for the external validation set. Radiographs from the external validation set had white lettering embedded, stating "PORTABLE" and "UPRIGHT" on the top corners of the images.

Images were resized to 256×256 pixels and base weights generated by training the model with an 80%/20% train/validation split.

To lessen the possibility of inadvertently creating a "PORTABLE/UPRIGHT" PA/AP radiograph detector, or PNG/JPG detector as a confounder, pre-processing of the images with sanity checks were utilized. As the larger embedded white lettering was not present in the training data nor the internal validation set, similar embedding on the internal validation set was digitally augmented. Additionally, occlusion mapping techniques were utilized, described subsequently. Additional testing of PNG and JPEG file formats confirmed that the DL model was not affected by the initial file format prior to conversion.

The internal validation set (internal COVID+ test set) included 413 patients that were seen between Mar. 17, 2020 and Oct. 24, 2020 and received both a CXR and positive real-time reverse transcription polymerase chain reaction (RT-PCR) COVID-19 test in the ambulatory or immediate care setting. Some of the patients went to the emergency department after the positive RT-PCR test, and some were hospitalized. The EHR clinical notes were reviewed to determine the reason and date of admission if any occurred.

The external validation set (external COVID+ test set) included 487 patients that were seen at a large urban tertiary academic hospital between Mar. 14, 2020 and Aug. 12, 2020 and received a frontal CXR in the emergency department and a positive RT-PCR COVID-19 test.

Clinical Data and Inclusion Criteria

Clinical variables included patient sex, age, mortality, morbidity, history of chronic obstructive pulmonary disease (COPD), diabetes with chronic complications, morbid obesity (body mass index [BMI]>40), congestive heart failure (CHF), cardiac arrhythmias, and vascular disease as determined by ICD10 codes. These common comorbidities were chosen as they are linked with HCC codes. The following HCCs were used: diabetes with chronic complications (HCC18), morbid obesity (HCC22), CHF (HCC85), specified heart arrhythmias (HCC96), vascular disease (HCC108), COPD (HCC111). Complete RAF scores, excluding age and sex, with the RAF score coefficients from the v23 model community, nondual-aged were used. Administrative RAF scores were calculated from ICD10 codes using Excel, excluding the demographic components. The calculated RAF score included all the available HCC coefficients for the patient, not just the six aforementioned HCC coefficients.

Figure 3A:
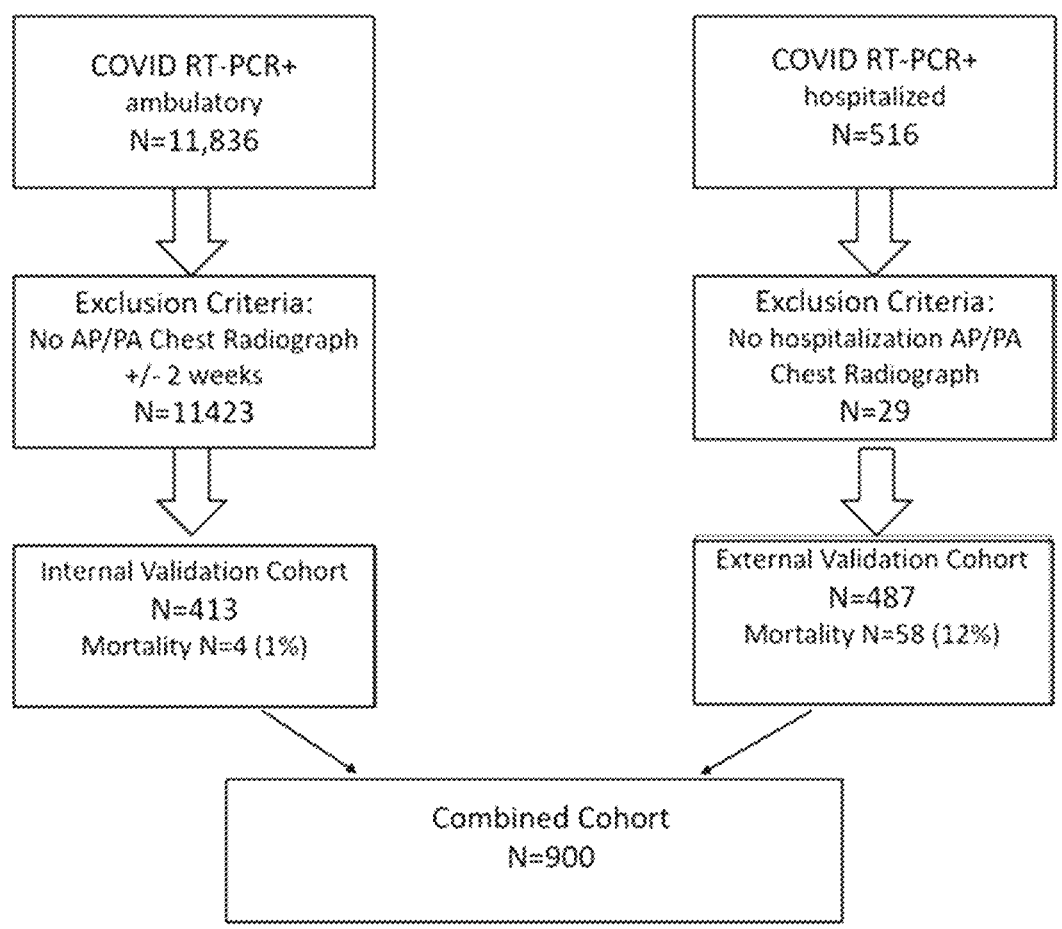
FIG. 3A illustrates a flowchart of an example method.

In cases of multiple RT-PCR COVID-19 tests, or negative and then positive tests, the first positive test was used as the reference date. In patients with multiple CXRs, only the radiograph closest to the first positive RT-PCR test was used (one radiograph per subject). Patients without locally available or recent CXRs, those with radiographs obtained more than 14 days from positive RT-PCR testing, and subjects less than 16 years of age at the time of radiography were excluded. Mortality was defined by death prior to discharge (this procedure is depicted as a flowchart in FIG. 3A). The outcome was determined by chart review in both cohorts.

Deep Learning

A multi-task multi-class CNN classifier was created by adapting a baseline standard ResNet34 classification model. The basic ResNet building block was modified by changing the 3×3 2D Convolution layer in the block to a 2D CoordConv layer to benefit from the additional spatial encoding ability of CoordConv. CoordConv allows the convolution layer access to its own input coordinates, using an extra coordinate channel. Using standard train/test/validation splits to isolate test data from validation data, the CoordConv ResNet34 model was first trained on publicly available CXR data from the CheXpert dataset and was then fine-tuned on local data using the internal anonymized outpatient frontal CXRs from 2010 to 2019.

Technical and hyperparameter details are as follows. The training was performed on a Linux (Ubuntu 18.04) machine with two Nvidia TITAN GPUs, with CUDA 11.0 (Nvidia) for 50 epochs over 10.38 hours. Training used image and batch sizes of 256×256 pixels and 64, respectively. All programs were run in Python (Python 3.6) and PyTorch (version 1.01). The CNN was trained by ADAM at a learning rate of 0.0005 with the learning rate decreased by a factor of 10 when the loss ceased to decrease for 10 iterations. Binary cross-entropy was used as the objective function for HCCs and sex classes, mean squared error for age and RAF classes. Data augmentation of images was performed with random horizontal flips (20%), random rotations (+/−10 degrees), crops (range 1.0, 1.1), zooms (range 0.75, 1.33), random brightness and contrast (range 0.8, 1.2), and skews (distortion scale of 0.2, with a probability 0.75). Images were normalized with the mean and standard deviation of the pixel values computed over the training set. The PIL library was used for image resizing of the initial JPEG and PNG files.

Positive pixel-based occlusion-based attribution maps were generated, using the Python library Captum 0.3.1, in which areas of the image are occluded and then used to quantify how the model's prediction changes for each class. A standard sliding window of size 15×15 with a stride of 8 in both image dimensions was used. At each location, the image was occluded with a baseline value of 0. This technique did not alter the DL model, but rather perturbed only the input image.

Statistical Analysis

Demographic characteristics and clinical findings were compared between the internal and external COVID+ cohorts using $\chi^2$ for categorical variables and t-tests for continuous variables. The predictions for age, RAF score, and six HCCs were compared to administrative data for the internal and external COVID+ cohorts to test the model's performance in predicting comorbidities. The analysis used AUC ROC. Age and RAF score were compared to the administrative data with correlation coefficients. The Spearman's rank correlation test was used to assess the similarity between the DL predictions and EHR for each medical condition and for RAF score. In Table 1 below, the eight AUCs were individually compared using the method of DeLong, and due to the use of multiple comparisons, the P values were adjusted using the method of Holm-Bonferroni, recall and precision values were also calculated.

TABLE 1

| Characteristic | Internal cohort AUC (95% CI) | External cohort AUC (95% CI) | P value |
| --- | --- | --- | --- |
| Sex | 0.94 (0.91-0.96) | 0.97 (0.95-0.98) | <.05 |
| Morbid obesity | 0.91 (0.88-0.95) | 0.86 (0.83-0.89) | .055 |
| Congestive heart failure | 0.84 (0.74-0.93) | 0.71 (0.65-0.76) | <.05 |
| Vascular disease | 0.87 (0.82-0.91) | 0.70 (0.64-0.75) | <.001 |
| Cardiac arrhythmias | 0.76 (0.66-0.86) | 0.74 (0.68-0.80) | .752 |

TABLE 1-continued

| Characteristic | Internal cohort AUC (95% CI) | External cohort AUC (95% CI) | P value |
|---|---|---|---|
| COPD | 0.85 (0.71-0.98) | 0.71 (0.63-0.78) | .075 |
| Diabetes with chronic complications | 0.77 (0.69-0.84) | 0.63 (0.58-0.68) | <.005 |
| All conditions | 0.85 (0.82-0.88) | 0.76 (0.73-0.78) | <.001 |

Multivariable logistic regression, backward elimination with fractional polynomial transformation, was performed with P<0.05 for inclusion of the variables from the DL model: sex, age, and six common ICD10 HCC codes (model v23). Feature selection was performed by selecting the ten most prevalent conditions and using backward elimination based on area under the receiver operating characteristic (ROC) curve (AUC) analysis discussed under statistical analysis.

Logistic regression with produced odds ratios (ORs) and 95% confidence intervals (CIs) for the outcomes of mortality on both COVID+ cohorts was performed. Model calibration was assessed graphically using nonparametric bootstrapping. The external cohort mortality model was then applied to the combined cohort. All tests were two-sided, P<0.05 was deemed statistically significant, and analysis was conducted in R version 4 (R Foundation for Statistical Computing, Vienna, Austria).

Results

Patient Characteristics

A total of 900 patients were included in the study: 413 (46%) from the internal COVID+ test set and 487 (54%) from the external COVID+ validation set (Table 2). The mean age of the internal cohort was 49.9 years (median=51, range=16-97, IQR=39); 221 were White (53%), 31 were Asian (7%), 96 were Hispanic (23%), 27 were African American (6.5%), and 38 were other or unknown (10%). In the internal cohort, there were 4 deaths.

TABLE 2

| Characteristic[a] | Internal validation (N = 413) | External validation (N = 487) | Comparative P Value |
|---|---|---|---|
| Age, mean (SD) | 49.9 (16.1) | 56.3 (16.4) | <.001 |
| Sex | | | .251 |
| Male | 222 (53.8%) | 242 (49.7%) | |
| Female | 191 (46.2%) | 245 (50.3%) | |
| Race | | | <.001 |
| White | 222 (53.8%) | 32 (6.6%) | |
| African American | 27 (6.5%) | 225 (46.2%) | |
| Hispanic | 93 (22.5%) | 59 (12.1%) | |
| Other | 46 (11.1%) | 165 (33.9%) | |
| BMI, mean (SD) | 30.8 (7.08) | 32.2 (10.1) | .011 |
| Mortality* | 4 (1.0%) | 58 (11.9%) | <.001 |
| Medical conditions per EHR | | | |
| Diabetes with complications | 44 (10.7%) | 172 (35.8%) | <.001 |
| Morbid obesity | 39 (9.4%) | 112 (23.3%) | <.001 |

TABLE 2-continued

| Characteristic[a] | Internal validation (N = 413) | External validation (N = 487) | Comparative P Value |
|---|---|---|---|
| Congestive heart failure | 11 (2.7%) | 104 (21.6%) | <.001 |
| Cardiac arrhythmias | 19 (4.6%) | 71 (14.8%) | <.001 |
| Vascular disease | 30 (7.3%) | 105 (21.8%) | <.001 |
| COPD | 7 (1.7%) | 57 (11.9%) | <.001 |
| RAF, mean (SD) | 0.246 (0.493) | 1.51 (1.66) | <.001 |
| Frontal chest radiograph DL outcomes | | | |
| Predicted age, mean (SD) | 53.2 (13.4) | 60.7 (10.4) | <.001 |
| Medical conditions, mean (SD)[b] | | | |
| Diabetes with complications | 0.182 (0.197) | 0.534 (0.208) | <.001 |
| Morbid obesity | 0.165 (0.250) | 0.353 (0.332) | <.001 |
| Congestive heart failure | 0.108 (0.161) | 0.426 (0.252) | <.001 |
| Cardiac arrhythmias | 0.080 (0.134) | 0.286 (0.221) | <.001 |
| Vascular disease | 0.237 (0.232) | 0.412 (0.212) | <.001 |
| COPD | 0.084 (0.146) | 0.136 (0.147) | <.001 |
| Predicted RAF, mean (SD) | 0.610 (0.463) | 1.451 (0.528) | <.001 |

The mean age of the external validation set was 56.3 years (median=57, range=18-95, IQR=45); 32 were White (6.6%), 225 were African American (46.2%), 59 were Hispanic (12.1%), and 165 were other (33.9%). In the external validation set, there were 58 deaths.

Training Cohort

A set of 11,257 anonymized unique frontal CXRs was used to train the CNN model previously described to predict patient sex, age, and six HCCs using administrative data. A randomly selected set of 2,864 (20%) radiographs was used as a first test set for initial model validation. The mean age at the time of the radiograph was 66±13 years; 43% of the radiographs were from male patients.

DL CNN Analysis

The DL model produces a probability (0-1) for patient sex and each predicted HCC comorbidity. These predictions were compared to the HCC administrative data for the baseline, internal, and external validation cohorts. For each HCC, the relationship for the DL test data is summarized by a ROC and AUC (Table 1).

AUC predictions for the internal COVID+ cohort for each HCC ranged from 0.94 to 0.75 (Table 1 internal validation). The total AUC for all HCCs was 0.85. The HCC predictions on the external COVID+ validation set were compared to administrative data to determine if the DL model was predictive. (Table 1, external validation). AUC ranged from 0.97 for sex to 0.63 for diabetes with chronic complications. The total AUC for all external validation cohort HCCs was 0.76. Comparisons were performed and no statistically significant differences were found for COPD, morbid obesity, and cardiac arrhythmias (Table 1). In regard to recall and precision (Table 3), values followed the same trend as AUC, in the internal COVID+ cohort precision ranged from 0.05 to 0.84, and precision from 0.68 to 0.95. The external COVID+ cohort precision and recall values ranged from 0.23 to 0.89 and 0.63 to 0.94, respectively.

TABLE 3

| Characteristic | Internal validation | | External validation | |
| --- | --- | --- | --- | --- |
| | Precision | Recall | Precision | Recall |
| Diabetes with chronic complications | 0.265 | 0.682 | 0.428 | 0.831 |
| Morbid obesity | 0.308 | 0.949 | 0.454 | 0.920 |
| Congestive Heart Failure | 0.079 | 0.909 | 0.382 | 0.625 |
| Cardiac Arrhythmias | 0.086 | 0.842 | 0.264 | 0.732 |
| Vascular Disease | 0.226 | 0.867 | 0.308 | 0.819 |
| COPD | 0.048 | 0.857 | 0.228 | 0.649 |
| All conditions | 0.166 | 0.800 | 0.364 | 0.752 |
| Gender | 0.844 | 0.928 | 0.884 | 0.942 |

The correlation coefficient (R) between predicted and administrative RAF score in the internal validation set was 0.43 and in the external cohort was 0.36. The mean absolute error for the predicted RAF score in the internal validation set was 0.49 (SD±0.39) and in the external dataset was 1.2 (SD±1.04). In the administrative data, RAF scores were zero in 57.9% (n=239) of the internal validation set patients (mean=0.25, range=0-4), and in 18.2% (n=89) of the external patients (mean=1.5, range 0-10).

Figure 3B:
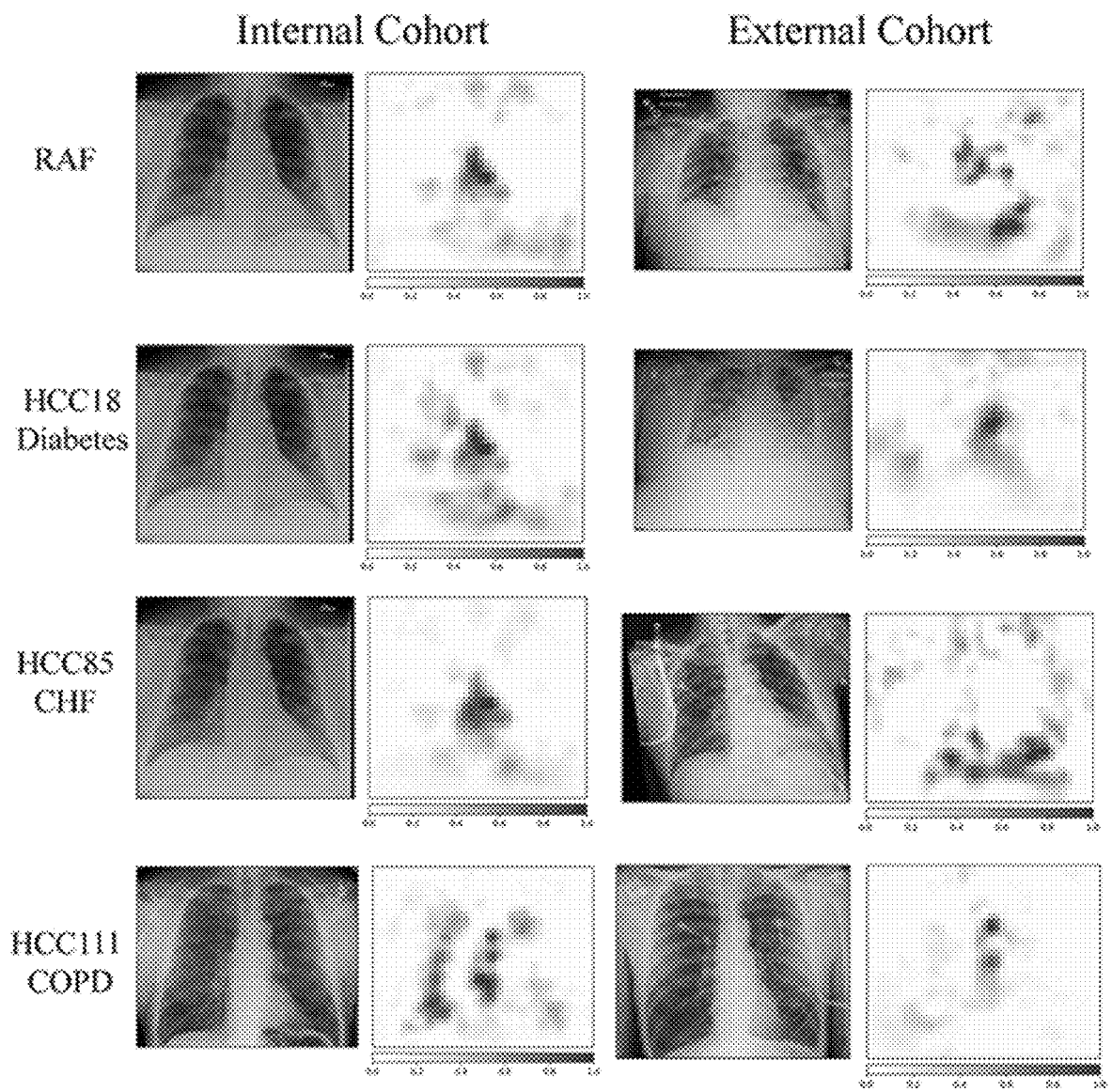
FIG. 3B illustrates experimental results.

Comparative and representative frontal CXRs from both internal and external COVID+ cohort patients are shown in FIG. 3B, which demonstrates how the DL model analyzed the radiographs and generated the likelihoods of comorbidities. Darker pixels in FIG. 3B indicate a location that when occluded changed the risk adjustment factor (RAF) score in top row. Each row of FIG. 3B represents the comorbidity and the resulting occlusion maps. Note that image labeling and electrodes did not impact the score. Qualitatively, the occlusion mapping demonstrated similar distributions in both even in the presence of artifacts such as image labels, electrodes, and rotated patient position. Additional paired t-testing of the internal validation set with augmented white text in the upper image corners did not generate a statistically significant difference at the P=0.05 level among all predictors. Additionally, paired t-testing was performed with input 8-bit PNG and 24-bit JPEG file formats, without a statistically significant difference at the P=0.05 level among all predictors.

Figure 3C:
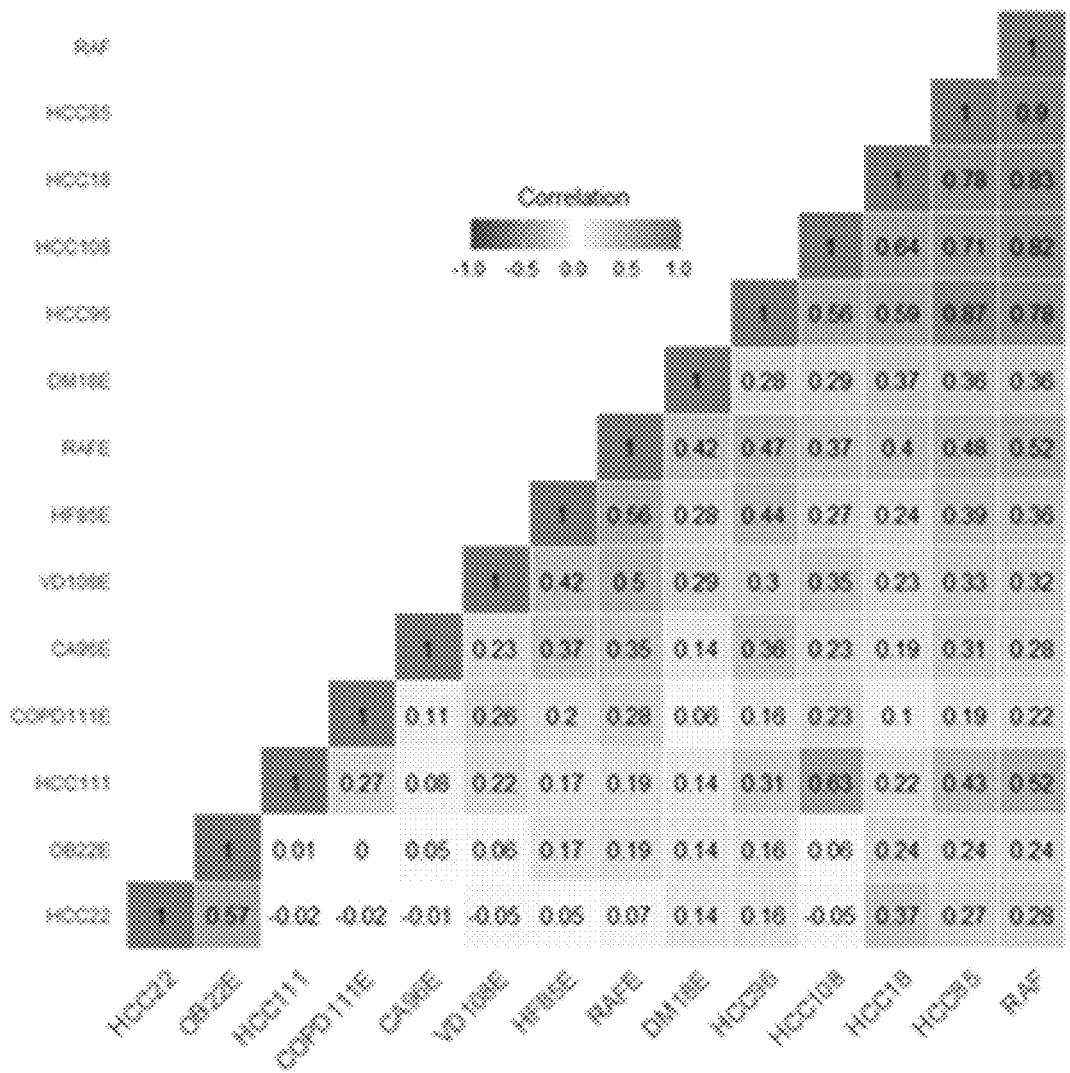
FIG. 3C illustrates experimental results.

FIG. 3C depicts the Spearman's rank correlation coefficients for each HCC and for RAF score for the EHR and the DL model for the entire dataset (DM18E=diabetes with complications, OBS22E=morbid obesity, HF85E=congestive heart failure, CA96E=cardiac arrhythmias, CA96E=vascular disease, COPD111E=chronic obstructive pulmonary disease, RAF=risk adjustment factor). Overall, comorbidities and the RAF score were positively correlated with each other, highlighting the comorbid nature of the chronic medical conditions evaluated, conditions with the highest correlation included being diagnosed with CHF, diabetes with chronic complications, vascular disease, heart arrhythmias and COPD. In addition, the RAF score from the DL model demonstrated good to strong correlation with five EHR covariables (0.52-0.9), consistent with the RAF score being a combination of HCCs.

Univariate and Multivariate Analysis

The external validation set patients were significantly older (mean age, 56.3 years±16.4 vs 49.9 years±15, P<0.001) but similar in obesity (BMI 32.2±10.1 vs 30.8±7.08, P=0.01) compared with the internal validation set patients. From EHR data, the external validation set patients all had a significantly greater prevalence of comorbidities, as would be expected in a hospitalized cohort. The DL model predictions were correspondingly significantly larger in the external validation set for all six HCCs.

Outcome Modeling on External Validation Cohort

After backward elimination, the following variables remained in the logistic regression model for the prediction of mortality in the external validation cohort: RAF predicted score (adjusted OR, 35; 95% CI: 10-120; P<0.001), HCC11 (COPD) prediction (adjusted OR, 0.02; 95% CI: 0.001-0.29, P=0.004), male sex predicted (adjusted OR, 2.9, 95% CI: 1.36-6.05; P<0.01), HCC85 prediction (CHF) (adjusted OR, 0.058; 95% CI: 0.006-0.563; P=0.01), and HCC18 prediction (diabetes with chronic complications) (adjusted OR, 0.07; 95% CI: 0.009-0.59; P=0.01) (Table 3). The AUC for this model was 0.76 (95% CI: 0.70-0.82). The model calibration had a slope of 0.92. Applying this logistic regression model on the combined internal validation and external validation cohorts (n=900) demonstrated an ROC AUC of 0.84 (95% CI: 0.79-0.88) for the prediction of mortality, indicating the model has generalizability. The ROC AUC of the internal validation cohort modeled similarly was 0.81 with a nonsensical confidence interval due to the low number of mortalities in the ambulatory cohort of patients.

Discussion

In this study a DL model was developed to predict select comorbidities and RAF score from frontal CXRs; this model was then externally validated using a VBC framework based on HCC codes from ICD-10 administrative data. Because it was recognized that the internal validation set was skewed towards less ill patients, with 4 deaths in the internal validation set, a corresponding dataset with more severe disease was sought to ascertain validity over a broad spectrum of patient presentations. The DL model demonstrated discriminatory power in both hospitalized external and ambulatory internal cohorts but was improved when operating on the full spectrum of patients as would be seen across a region of practice with multiple different care settings and degrees of patient illness. These combined cohorts together represented the full spectrum of COVID+ disease from ambulatory to moribund. The covariables derived from the initial frontal CXRs of an external cohort of patients admitted with COVID-19 diagnoses were predictive of mortality.

The use of comorbidity indices derived from frontal CXRs has many potential benefits and can serve a dual role in VBC by identifying patients with an increased risk of mortality and therefore healthcare expenditures. Radiology's role in VBC has been frequently questioned, and imaging biomarkers, such as RAF scores determined from CXRs via the methods described herein, offer unique opportunities to identify undocumented, under-diagnosed, or undiagnosed high-risk patients. Increasingly, "full risk" VBC models require healthcare systems to bear financial responsibility for patients' negative outcomes, such as hospitalizations. Radiologists currently may be unfamiliar with RAF scoring; however, US clinicians are increasingly aware because of the Medicare Advantage program and the associated reimbursement implications. In the developed logistic regression model of the DL covariables, RAF score was a strong predictor of mortality; similarly, pre-existing administrative data is predictive of COVID-19 outcomes and hospitalization risk.

Many challenges exist within the fragmented US healthcare system, particularly in the utilization of medical administrative data. Since CXRs are frequently part of the initial assessment of many patients, including those with COVID-19, comorbidity scores predicted from CXRs could be rapidly available for and help clinicians with prognosis. A significant percentage of patients in both cohorts were found who had RAF scores of 0 (excluding the demographic components), which could signify the absence of documented disease, or the absence of medical administrative data at the respective institution. However, there are conditions in the VBC HCC model that are difficult to confidently associate with a CXR, like major depression, and such a score could be viewed as only a portion of a more comprehensive evaluation of the patient.

There are numerous clinical models of outcomes in COVID-19, many focused on admitted and critically ill hospitalized patients. Several models have utilized the CXR as a predictor of mortality and morbidity for hospitalized COVID-19 patients, based on the severity, distribution, and extent of lung opacity. Features of the CXR other than those related to airspace disease can aid in prognostic prediction in COVID-19. In addition, a significant number of COVID-19 patients demonstrate subtle or no lung opacity on initial radiographic imaging, more likely early in the disease course and ambulatory setting, potentially limiting airspace-focused models.

The DL model described herein facilitated the generation of predictions regarding the probabilities of comorbidities such as morbid obesity, diabetes, CHF, arrhythmias, vascular disease, and COPD; those were correlated with EHR diagnosis. Although these DL scores do not replace traditional diagnostic methods (i.e., HbA1c, BMI), they were predictive using the standard of EHR HCC codes. A heatmap of Spearman's correlation coefficient (FIG. 3C) between external and internal predictors from the DL model demonstrates that the RAF score is an amalgamation of the other comorbidities scores, and is strongly correlated to cardiovascular predictors, such as CHF (HCC85) and vascular disease (HCC108).

The DL model's performance was diminished in the external cohort, as seen by lower AUCs in several prediction classes. Reasons for this may include differences in disease prevalence in the populations, institutional differences in documenting disease, external artifacts, and potential differences based on race, ethnicity, socioeconomic factors. One clear difference between the training and internal validation cohort as compared to the external validation cohort was that the CNN was trained on PA CXRs, and the internal cohort used PA radiographs, but the external cohort had less than 10% PA CXRs. It is likely that the CNN would have performed better on the external COVID+ patients if the CNN had been trained on similar patients using PA CXRs. However, despite all these differences, the DL model maintained discriminatory ability.

Occlusion maps (FIG. 3B) did not demonstrate significant attribution to external artifacts, such as image markers, with overall similar patterns of attribution between the two cohorts per class. The occlusion mapping in these cohorts demonstrates positive attribution to the cardiovascular structures for the RAF score, such as the heart and aorta, which was a strong predictor for mortality in the external cohort. Whereas in the prediction for COPD (HCC111) the hyperinflated lung parenchyma and a narrow mediastinum are predominant features on occlusion mapping (FIG. 3B), similar to what a radiologist would observe. The prediction of diabetes utilizes body habitus at the upper abdomen, axillary regions, and lower neck (FIG. 3B), which is strongly associated with type II diabetes. Using logistic regression on the DL model's predictions in the external cohort against mortality demonstrated ROC AUC values that were comparable to other studies. This logistic regression model, when applied to both cohorts demonstrated an increased ROC AUC, as the internal cohort had less disease findings, similarly described by Schalekamp.

In conclusion, a multi-task CNN DL model of comorbidities derived from VBC-based administrative data was able to predict 6 comorbidities and mortality in an ambulatory COVID+ cohort as well as an inpatient COVID+ cohort. In addition, these model covariables, especially the VBC-based predicted RAF, can be used in logistic regression to predict mortality without any additional laboratory or clinical measures. This result suggests further validation and extension of this particular methodology for potential use as a clinical decision support tool to produce a prognosis at the time of the initial CXR in a COVID+ patient, and perhaps more generally as well.

VI. DETECTING RACIAL/ETHNIC HEALTH DISPARITIES USING DEEP LEARNING FROM FRONTAL CHEST RADIOGRAPHY

Value Based Care can be impacted when evaluating imaging biomarkers and social determinants of health detected through deep learning algorithms.

A deep learning chest radiograph classifier as described herein was predictive for thoracic atherosclerotic vascular disease in patients with coronavirus disease 2019 as compared to presence of the administrative code for vascular disease in electronic health records.

The discrepancy between the classifier predictions and coded vascular disease demonstrated significant associations with race/ethnicity, social deprivation index (SDI) and language preference. This discrepancy was associated with an at-risk cohort with higher mean SDI, but not a more affluent cohort with lower mean SDI. This may mean that social deprivation must surpass a threshold before impact. Furthermore, absence of coded thoracic vascular disease, even when controlled for age, sex, race, and language was itself suggested as a potential marker for underdiagnosis or underdocumentation.

A CNN model as described herein was trained to predict atherosclerotic disease from ambulatory frontal CXRs (chest radiographs). The model was then validated on two cohorts of COVID-19 patients: 814 ambulatory patients from a suburban location (presenting Mar. 14, 2020 to Oct. 24, 2020, the internal ambulatory cohort) and 485 hospitalized patients from an inner-city location (hospitalized Mar. 14, 2020 and Aug. 12, 2020, the external hospitalized cohort). The CNN model predictions were validated against electronic health record (EHR) administrative codes in both cohorts and assessed using the area under the receiver operating characteristic (ROC) curves (AUCs). The CXRs from the ambulatory cohort were also reviewed by two board-certified radiologists and compared to the CNN-predicted values for the same cohort to produce an ROC and AUC. The atherosclerosis diagnosis discrepancy, $\Delta_{vasc}$, was calculated as the difference between the CNN-predicted value and the presence or absence of the administrative code. Linear regression was used to determine the association of $\Delta_{vasc}$ with the covariates of age, sex, race/ethnicity, language preference and social deprivation index (SDI).

Logistic regression was also used to look for an association between the absence of the administrative code and $\Delta_{vasc}$ and other covariates.

The CNN prediction for vascular disease from frontal CXRs in the ambulatory cohort had an AUC of 0.85 (95% confidence interval (CI)=0.82-0.89) and in the hospitalized cohort had an AUC of 0.69 (95% CI=0.64-0.75) against the EHR data. In the ambulatory cohort, the consensus radiologists' reading had an AUC of 0.97 (95% CI=0.96-0.99) relative to the CNN. Multivariate linear regression of $\Delta_{vasc}$ in the ambulatory cohort demonstrated a significant negative association with non-English language preference (P<0.05) and Black or Hispanic race/ethnicity (P<0.05) and a strong positive association with age (P<0.001) and sex (P<0.05). For the hospitalized cohort, age was also a strong factor (P<0.01), as was SDI (P<0.05). The $\Delta_{vasc}$ variable (odds ratio (OR)=0.34), Black or Hispanic race/ethnicity (OR=1.58), non-English language preference (OR=1.74) and site (OR=0.22) were independent predictors of the absence of the administrative code (all P<0.01) in the combined patient cohort The CXR classifier, determined as described herein, was predictive of aortic atherosclerosis in two cohorts (one ambulatory and one hospitalized) with COVID-19. For the ambulatory cohort, the correlation between the prediction and expert reading was excellent. Also, the discrepancy between the CNN model and the administrative code, $\Delta_{vasc}$, was associated with language preference in the ambulatory cohort; in the hospitalized cohort, this discrepancy was associated with SDI. The absence of the administrative code was associated with $\Delta_{vasc}$ in both the individual and combined cohorts, suggesting that $\Delta_{vasc}$ is an independent predictor of health disparities in Black or Hispanic patients. This may suggest that biomarkers extracted from routine imaging studies and compared with EHR data could play a role in enhancing Value-Based Healthcare for traditionally underserved or disadvantaged patients where barriers to care exist.

VII. PREDICTING PROLONGED HOSPITALIZATION AND SUPPLEMENTAL OXYGENATION IN PATIENTS WITH COVID-19 INFECTION FROM AMBULATORY CHEST RADIOGRAPHS USING DEEP LEARNING

Supervised multi-task deep learning with convolutional neural networks (CNNs) on frontal chest radiographs as described herein was able to predict many underlying patient comorbidities represented by hierarchical condition categories (HCCs) from the International Classification of Diseases, Tenth Revision, including those corresponding to diabetes with chronic complications, morbid obesity, congestive heart failure, cardiac arrhythmias, and chronic obstructive pulmonary disease. Using submitted HCC codes to train and test the CNNs, among all predicted comorbidities, the total area under the receiver operating characteristic (ROC) curve (AUC) was 0.856 (95% CI: 0.845-0.862), with individual AUCs ranging between 0.729 and 0.927.

Combining the multi-task CNN output with patient age and two standardized COVID-19 airspace disease predictors in 413 outpatients testing positive for COVID-19, a standard frontal chest radiograph predicted hospitalization of >2 day's duration and supplemental oxygenation with an ROC AUC of 0.837 (95% CI: 0.791-0.883), independent of additional clinical and laboratory data.

The clinical prognosis of outpatients with COVID-19 remains difficult to predict, with outcomes including asymptomatic, hospitalization, intubation, and death. The prognostic value of an outpatient chest radiograph was determined using an ensemble of deep learning algorithms predicting comorbidities and airspace disease to identify patients at a higher risk of hospitalization from COVID-19 infections.

This retrospective study included outpatients with COVID-19 confirmed by reverse transcription-polymerase chain reaction testing who received an ambulatory chest radiography between Mar. 17, 2020 and Oct. 24, 2020. In this study, full admission was defined as hospitalization within 14 days of the COVID-19 test for >2 days with supplemental oxygen. Univariate analysis and machine learning algorithms were used to evaluate the relationship between the deep learning model predictions and hospitalization for >2 days.

The study included 413 patients, 222 men (54%), with a median age of 51 years (interquartile range, 39-62 years). Fifty-one patients (12.3%) required full admission. A boosted decision tree model produced the best prediction. Variables included patient age, frontal chest radiograph predictions of morbid obesity, congestive heart failure and cardiac arrhythmias, and radiographic opacity, with an internally validated area under the curve (AUC) of 0.837 (95% CI: 0.791-0.883) on a test cohort.

Deep learning analysis of single frontal chest radiographs was used to generate combined comorbidity and pneumonia scores that predict the need for supplemental oxygen and hospitalization for >2 days in patients with COVID-19 infection with an AUC of 0.837 (95% confidence interval: 0.791-0.883). Comorbidity scoring may prove useful in other clinical scenarios.

The COVID-19 pandemic placed unprecedented demand on healthcare systems. Although many infected individuals have mild or no symptoms, some become very ill and may be hospitalized for long durations. Comorbid conditions like diabetes and cardiovascular disease are associated with more severe cases of COVID-19. Unfortunately, relevant comorbidities are sometimes unknown or unrecognized by the medical provider and patient, limiting the provider's ability to perform a proper risk assessment. Previously, the extraction of comorbidity data was based on contemporaneously provided patient history, manual record review, and/or electronic health record (EHR) queries, and the results were imperfect and often incomplete. The work described herein developed a deep learning algorithm that could predict the likely presence of relevant comorbidities, in combination with an algorithm to quantify opacity, from frontal chest radiographs (CXRs), enabling providers to more effectively risk-stratify patients presenting with COVID-19 infection.

COVID-19 infection is diagnosed with reverse transcription-polymerase chain reaction (RT-PCR) or antigen tests. In patients with limited symptoms, additional testing is often unnecessary. In patients with higher risk for severe disease or complications, however, including those presenting with more severe symptoms, chest radiography is widely used for evaluation.

The Centers for Medicare and Medicaid Services uses a specific subset of hierarchical condition category (HCC) codes from the International Classification of Diseases, Tenth Revision (ICD10) to model chronic disease comorbidities and their associated costs of care for value-based payment models. The codes are generated through encounters with healthcare providers and recorded in administrative data. These data elements are often more reproducible and more amenable to query as compared to broader searching of EHR systems. Using a convolutional neural network (CNN) as described herein to link these categorical codes to a CXR can convert the images into useful biomarker proxies for a patient's chronic disease burden. For instance, a high categorical prediction for HCC18 would indicate that a CXR strongly suggests diabetes with chronic complications.

Patient Cohort and Clinical Setting

The two cohorts in this study comprise patients receiving an outpatient frontal CXR at a large multi-specialty medical group. The first cohort consists of 14,121 CXRs of patients from 2010 to 2019, who were enrolled in the Medicare Advantage program. These patients had CXRs for typical clinical indications, like pneumonia, chest pain, and cough. None of these patients had COVID-19 infection, because of the relatively small number of available COVID patients, making it difficult to obtain an adequate distribution of comorbidities to train a neural network. This cohort was used to develop and validate a multi-task CNN to predict HCC-based comorbidities.

The second cohort was seen between Mar. 17, 2020 and Oct. 24, 2020 and received both a CXR and a positive RT-PCR COVID-19 test in the ambulatory or immediate care setting. Some of the patients went to the emergency department after the positive RT-PCR test and some were hospitalized. The EHR clinical notes were reviewed for information regarding the reason, date of admission, treatments, and length of hospitalization in days. This cohort is called COVID+. "Full admission" was defined as hospitalization >2 days with supplemental oxygen.

In cases of multiple positive COVID-19 RT-PCR tests, or negative and then positive tests, the first positive test was used as the reference date. Likewise, in patients with multiple outpatient CXRs, the radiograph closest to the initial positive RT-PCR was used, with only one radiograph used per subject. Patients without locally available or recent CXRs, radiographs obtained >14 days after positive RT-PCR testing, and subjects <16 years old at the time of radiography were excluded. Patients admitted for >2 days within 14 days of the RT-PCR test and 7 days of chest radiography were defined as full admissions.

Image Acquisition and Analysis

All radiographs were obtained conventionally with digital posteroanterior radiography; no portable radiographs were included. All CXRs were extracted from the PACS system utilizing a scripted method (SikuliX, 2.0.2) and saved as de-identified 8-bit grayscale portable network graphics (PNG) files.

Deep Learning

A multi-task CNN was trained on anonymized outpatient frontal CXRs from 2010 to 2019 randomly split into 80% training and 20% test data sets. The ground truth labels were the associated EHR ICD10 codes. The 80% set was trained on gender, age, and six common ICD10 HCC codes (model v23, used by the Centers for Medicare and Medicaid Services). ICD10 codes were obtained via queries of the EHR (Epic) from the transactions table. The following HCC categories were used: diabetes with chronic complications (HCC18), morbid obesity (HCC22), congestive heart failure (CHF; HCC85), specified heart arrhythmias (HCC96), vascular disease (HCC108), and chronic obstructive pulmonary disease (COPD; HCC111). In the training set, each radiographic file was a separate row, with the absence of any associated ICD10 HCC codes labeled as 0, and the presence of one or more codes labeled as 1.

Binary cross-entropy was used as the objective function in PyTorch (version 1.01), and the ADAM optimizer with a learning rate of 0.0005 was used to train the neural network. The learning rate was decreased by a factor of 10 when the loss ceased to decrease for 10 iterations. Random horizontal flips (20%), random affine (rotate image by max of 10 degrees), random resized crop scale (range 1.0, 1.1), ratio (range 0.75, 1.33), and random perspective (distortion scale of 0.2, with a probability 0.75) modifications were applied for data augmentation. Image normalization was performed by using the standard PyTorch function, with the mean and standard deviation of the pixel values computed over the training set. For image resizing, the PIL library was used to downscale to 256×256 with the Lanczos filter. A customized CoordConv ResNet34 model was pretrained on the CheXpert dataset; CoordConv allows the convolution layer access to its own input coordinates, using an extra coordinate channel. The training was performed on a Linux (Ubuntu 18.04) with two Nvidia TITAN GPUs, with CUDA 11.0 (Nvidia) for 50 epochs over 10.38 hours. Training used image and batch sizes of 256×256 and 64, respectively. All programs were run in Python (Python 3.6).

Multi-Task Learning (MTL)

MTL is a general framework for learning several tasks simultaneously using their shared structure. In contrast to standard (single-task) learning where each task is learned independently, MTL exploits inter-task relationships to improve the representation and prediction quality. MTL can be implemented using various approaches, including explicit parameter sharing and implicit parameter sharing (e.g., using nuclear norm regularization). When individual task performance improves, this is known as "positive transfer" and indicates that joint learning is superior to separate learning. In contrast, though less common, individual task performance can degrade with MTL, a "negative transfer" phenomenon.

To quantify the geographic extent and severity of opacity of infection, the open-source program COVID-Net was used, which produces two scores: one for the geographic extent and one for the severity of opacity. Both scores were normalized from 0 to 1.

Clinical Data

Clinical variables evaluated included patient age, gender and length of stay. History of COPD, diabetes, morbid obesity (body mass index [BMI]>40), CHF, cardiac arrhythmias, or vascular disease was determined by ICD10 ambulatory billing codes. Other than the COVID-19 RT-PCR test, outpatient lab results were not used, as most were unavailable within 24 hours of the COVID-19 RT-PCR positive test.

Statistical Analysis

One-to-one comparison of categorical and continuous variables was done with logistic regression. The t-test was not used as many of the variables were nonparametric. The predictions for the six HCCs were compared to the COVID+ cohort billing claims to test that this model, derived from a large cohort of patients prior to the COVID-19 pandemic, had predictive power with the COVID+ cohort. The analysis used the area under the curve (AUC) of receiver operating characteristic (ROC) curves. No hypothesis testing was done. Logistic regression produced odds ratios with 95% confidence intervals (CIs). All tests were two-sided, a P value <0.05 was deemed statistically significant, and analysis was conducted in R version 4.

Fit of Radiographic Features to Outcome Data

The COVID+ cohort had 11 input features and 1 outcome: whether or not a patient had a full admission (>2 days) within 7 days of the CXR. To assess the contributions and performance of the six-variable HCC CNN model and the two-variable geographic extent and opacity severity model, separate logistic regressions and AUC curves were generated and compared, with k-fold cross-validation accuracies also calculated. The data were split into a training/validation set (70%) and a testing set (30%). Several machine learning models, including logistic regression, decision trees, random forest, XGBoost, LightGBM, and CatBoost, were developed and optimized in Python (Python 3.6) using the training/validation set. The model development process used recursive feature elimination to find the optimal feature set for each model. In this approach, a single feature was removed at each step and the model was evaluated on the validation set. The quality of the fits to the data were measured using the ROC AUC. The best model was tested against the testing set for a final measure of prediction.

Results

Patient Characteristics

In total, 413 patients were included in the COVID+; 221 were White [53%], 31 were Asian [7%], 96 were Hispanic [23%], 27 were Black [6.5%], and 38 were other or unknown [10%]. Fifty-one (12%) of the patients had a full admission, with all requiring supplemental oxygen, and four died. No deaths were recorded within 48 hours of admission. Their mean age was 60 years (±13, median=58, range=39-97), 54% were male, and they had a mean length of stay of 10 days (±9, median=7, range=3-45). Patients without a full admission had a mean age of 48 years (±15, median=49, range=16-89) and 53% were male.

CNN Analysis

A set of 14,121 anonymized unique frontal CXRs (compliant with the Health Insurance Portability and Accountability Act) was used to train a CNN to predict six HCCs using ambulatory billing data. The CNN was also trained to predict the age of the patient. The mean age of the patients, at the time of the radiograph, was 66±13 years, and 57% of the patients were women. First, a training set of 11,257 (80%) radiographs was used to develop the CNN, which was then tested against a randomly selected set of 2,864 (20%) radiographs.

The CNN produced a probability for each predicted variable including age, diabetes with chronic complications (HCC18), morbid obesity (HCC22), CHF (HCC85), vascular disease (HCC108), and COPD (HCC111). This could be compared to the HCC data for the test cohort. For each variable, the relationship is summarized by a ROC.

Because the CNN was trained on a cohort selected from all ambulatory frontal CXRs prior to 2020, we compared the HCC predictions on the COVID+ cohort to determine whether the CNN was predictive in this clinical setting. All saliency maps were generated in Python, with the integrated gradients attribution algorithm, which computes the integral of the gradients of the output prediction for the class index, with respect to the input image pixels. Importantly, this technique does not modify the CNN model.

Imaging Characteristics of the COVID+ Cohort

The COVID-Net deep learning model was applied to quantify the extent and degree of opacity, which generates geographic and opacity (geographic-opacity) scores, normalized from 0 to 1. For full admission, the average geographic scores were 0.26±0.01 (median=0.22), and average opacity scores were 0.41±0.12 (median=0.39), while for those without full admission, scores were 0.21±0.05 (median=0.19) and 0.34±0.08 (median=0.31), respectively.

Univariate and Multivariate Analysis

Information on the COVID+ cohort was divided by presence or absence of a full admission. Patients with full admissions were significantly older (mean age, 60 years±13 vs. 48 years±15, P<0.0001). Univariate analysis demonstrated that the frontal CXR comorbidity model predictions generated for diabetes with chronic complications, cardiac arrhythmias, CHF, COPD, predicted age, and geographic extent and severity of opacity were all significant predictors (P<0.05), while morbid obesity was not.

Binary classification logistic regressions of the predicted six-variable CNN HCC model, geographic-opacity model, and combined eight-variable model were plotted as ROC curves, excluding patient age, against the entire COVID+ cohort. The fit for the HCC model had an AUC of 0.768 (95% CI: 0.708-0.829), the geographic-opacity model had an AUC of 0.693 (95% CI: 0.611-0.776), and the combined model had an AUC of 0.796 (95% CI: 0.734-0.859). The AUC for just the binomial EHR-based ICD10 HCC codes was 0.5646 (95% CI: 0.507-0.6221). Utilizing the method of DeLong to compare the AUCs of the combined and geographic-opacity regression models demonstrated a statistically significant difference, with a P value of 0.001.

The patient's age, comorbidities predicted by the CNN, and airspace disease (geographic-opacity scores) measured by the COVID-Net deep learning model were used to model the likelihood of a full admission. A development cohort (N=216) and validation cohort (N=73) were first used to produce models using different methods, and these were tested against a 30% test cohort (models outlined in methods). The two best methods for prediction on the development/validation cohort were logistic regression (AUC 0.81) and XGBoost (AUC 0.94). The XGBoost model was then used to model the remaining independent 30% test cohort. The final fit had an AUC of 0.837 (95% CI: 0.791-0.883). This model required five variables for prediction; the five variables used were age, opacity, and CNN-derived HCCs for morbid obesity, CHF, and specified heart arrhythmias.

Discussion

In this an ensemble deep learning model as described herein was developed to predict supplemental oxygenation and hospitalization of >2 days in outpatients testing positive for COVID-19. This model was based only on patient age and a conventional outpatient frontal CXR image obtained before admission in 413 patients and showed an AUC of 0.837 (95% CI: 0.791-0.883), with a boosted random forest method. There is a complementary benefit of the ensemble deep learning models when predicting comorbidities and predicting geographic extent and severity of opacity on CXRs, as demonstrated by comparison of the AUCs.

The learning technique described herein adds value when assessing patients with unknown medical history or awaiting laboratory testing. A significant number of COVID-19 patients demonstrate little to no abnormal lung opacity on initial radiographic imaging, and comorbidity scoring is beneficial in these patients when infection might be in the early stages. Additionally, comorbidity scoring could be helpful in identifying patients who could benefit from earlier initiation of treatment such as antibody therapy or close clinical surveillance.

The deep learning techniques described herein facilitated predictions regarding the probabilities of comorbidities such as morbid obesity, diabetes, CHF, arrhythmias, vascular disease and COPD. Although these results may have best clinical effect in combination with traditional diagnostic methods (i.e., glycated hemoglobin, BMI), it was found that they were predictive using the gold standard of ICD10 HCC administrative codes, with all the AUC confidence intervals well above 0.5, demonstrating a predictive value. When tested on an entirely different cohort, the COVID+ patients, the prediction similarly demonstrated AUCs well above 0.5, even in those with low opacity scores. Lastly, when using binary classification logistic regression from the combination of CNN models on the COVID+ cohort, a 'lift' of the combined model AUC was observed, with a statistically significant difference (P=0.001).

These HCC predictions were combined with quantitative predictions on lung opacity and patient age, and the resulting model had discriminatory ability in predicting which ambulatory patients would require full admission within 14 days of the positive RT-PCR test. Interestingly, morbid obesity was not significant in the univariate analysis but was significant in the multivariate analysis, suggesting Simpson's paradox, where the correlation is changed when the variables are combined. The final model used three of the HCC predictions to help classify patients, and thus, even if the predictions are not entirely mapped to a comorbidity, the resulting measurement strongly correlates and has significance for hospitalization due to COVID-19.

In this study on ambulatory patients, a minority had timely and complete laboratory assessments, unlike hospitalized patients who typically undergo extensive testing at presentation, limiting the ability to use laboratory results. Many of these laboratory markers are not widely available or are expensive.

The use of comorbidity indices derived from frontal CXRs has many potential benefits. In many acute clinical settings, comorbidities may be undocumented or unknown at the time of presentation. The amount of time needed to take a full history can sometimes be an impediment, especially with high patient volumes seen during the pandemic. Since a CXR is a frequent part of the initial assessment of a COVID-19 patient, the predicted comorbidity scores could be rapidly available for all patients. Additionally, the EHR provides a predominately binomial system of documenting disease (present or absent), but not all patients have the same burden of disease, as in diabetes for instance. It is possible that a model like this one could help distinguish these differences.

Many of the models used for the prognosis of COVID-19-positive patients look at patients already hospitalized and attempt to predict clinical deterioration, intensive care unit admission, death, or some combination. When internally tested on their own data, the AUCs reported in the literature can be over 0.9 but often do not use an independent test set, which increases the risk of overfitting and obtaining an artificially high AUC. Numerous models have AUCs lower than 0.8, with most models ranging between 0.8 and 0.9. These models are often dependent on the EHR data to make their predictions, but missing data from the EHR can adversely model predictions, meaning a model from a single source like CXRs can add significant value.

The MTL deep learning model of comorbidities and geographic extent and severity of opacity described herein was predictive of prolonged hospitalization and supplemental oxygenation based on a single outpatient frontal CXR.

VIII. CONCLUSION

It should be understood that arrangements described herein are for purposes of example only. As such, those skilled in the art will appreciate that other arrangements and other elements (e.g. machines, interfaces, operations, orders, and groupings of operations, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and implementations have been disclosed herein, other aspects and implementations will be apparent to those skilled in the art. The various aspects and implementations disclosed herein are for purposes of illustration and are not intended to be limiting, with the true scope being indicated by the following claims, along with the full scope of equivalents to which such claims are entitled. It is also to be understood that the terminology used herein is for the purpose of describing particular implementations only, and is not intended to be limiting.

We claim:

1. A computer-implemented method comprising:
    receiving a target radiographic image of a chest of a subject, wherein the subject has a specified disease or syndrome, wherein an artificial neural network (ANN) has a set of inputs and a set of outputs, wherein the ANN has been trained by a training set including a plurality of radiographic images containing features that are mapped to the set of inputs and associated with labeled values mapped to the set of outputs, wherein a subset of the radiographic images contain instances of the features that are indicative of at least one comorbidity within a particular comorbidity class and are associated with instances of the labeled values that represent the particular comorbidity class, wherein the ANN a common layer and a plurality of parallel output heads, wherein the common layer provides outputs to the plurality of parallel output heads, and wherein each output head of the plurality of parallel output heads generates, as an output, a respective one of the set of outputs;
    applying the ANN to the target radiographic image to generate a set of target outputs for the target radiographic image, wherein output values of the set of target outputs indicate that the subject has at least one comorbidity in the particular comorbidity class;
    based on the set of target outputs for the target radiographic image, predicting at least one of (i) a degree of severity of the specified disease or syndrome or (ii) an amount of care that the subject will receive related to the specified disease or syndrome;
    based on the set of target outputs for the target radiographic image, predicting a likelihood that the subject has a specified disease or syndrome;
    determining that the likelihood that the subject has the specified disease or syndrome has an intermediate value; and
        responsive to determining that the likelihood that the subject has the specified disease or syndrome has an intermediate value, performing an additional diagnostic test on the subject to determine whether or to what degree the subject has the specified disease or syndrome.

2. The method of claim 1, wherein a further subset of the radiographic images contain no instances of the features that are indicative of any comorbidity within the particular comorbidity class and are not associated with any instances of the labeled values that represent the particular comorbidity class.

3. The method of claim 1, wherein a subset of the radiographic images are associated with instances of the labeled values that represent one or more of (i) at least one comorbidity within a first comorbidity class that encompasses diabetes with chronic complications, (ii) at least one comorbidity within a second comorbidity class that encompasses morbid obesity, (iii) at least one comorbidity within a third comorbidity class that encompasses congestive heart failure, (iv) at least one comorbidity within a fourth comorbidity class that encompasses specified heart arrhythmias, (v) at least one comorbidity within a fifth comorbidity class that encompasses vascular disease, or (vi) at least one comorbidity within a sixth comorbidity class that encompasses chronic obstructive pulmonary disease.

4. The method of claim 1, wherein a subset of the radiographic images are associated with instances of the labeled values that represent one or more of (i) at least one comorbidity within ICD10 hierarchical condition category HCC18, (ii) at least one comorbidity within ICD10 hierarchical condition category HCC22, (iii) at least one comorbidity within ICD10 hierarchical condition category HCC85, (iv) at least one comorbidity within ICD10 hierarchical condition category HCC96, (v) at least one comorbidity within ICD10 hierarchical condition category HCC108, or (vi) at least one comorbidity within ICD10 hierarchical condition category HCC111.

5. The method of claim 1, wherein the labeled values mapped to the set of outputs include a numerical output that is indicative of an overall degree of medical risk.

6. The method of claim 5, wherein the numerical output that is indicative of an overall degree of medical risk is a risk adjustment factor (RAF) score.

7. The method of claim 1, wherein the labeled values mapped to the set of outputs represent, respectively, whether respective subjects represented in respective radiographic images of the plurality of radiographic images have: (i) at least one comorbidity within ICD10 hierarchical condition category HCC18, (ii) at least one comorbidity within ICD10 hierarchical condition category HCC22, (iii) at least one comorbidity within ICD10 hierarchical condition category HCC85, (iv) at least one comorbidity within ICD10 hierarchical condition category HCC96, (v) at least one comorbidity within ICD10 hierarchical condition category HCC108, or (vi) at least one comorbidity within ICD10 hierarchical condition category HCC111.

8. The method of claim 7, wherein the labeled values mapped to the set of outputs additionally include a risk adjustment factor (RAF) score.

9. The method of claim 1, further comprising:
applying a plurality of different modified versions of the target radiographic image to the ANN to generate a visual map that depicts a region within the target radiographic image that is indicative of the at least one comorbidity within the particular comorbidity class, wherein each one of the different modified versions of the target radiographic image has a respective different region of the target radiographic image blanked.

10. The method of claim 1, further comprising:
applying the ANN to a particular radiographic image of the plurality of radiographic images of the training set to generate an updated set of outputs for particular radiographic image; and
updating the training set such that the particular radiographic image is associated with instances of the labeled values that reflect the updated set of outputs.

11. The method of claim 1, further comprising:
receiving a pre-determined set of outputs for the target radiographic image, wherein output values of the pre-determined set of outputs for the target radiographic image indicate that the subject does not have at least one comorbidity within the particular comorbidity class;
determining that the pre-determined set of outputs for the target radiographic image differs from the set of target outputs generated by the ANN with respect to the subject having at least one comorbidity within the particular comorbidity class; and
responsively providing an indication via a user interface that the pre-determined set of outputs for the target radiographic image differs from the set of target outputs generated by the ANN.

12. The method of claim 1, wherein the labeled values mapped to the set of outputs include a numerical output that is indicative of an overall degree of medical risk, and wherein the method additionally comprises:
receiving a pre-determined numerical indication of the overall degree of medical risk of the subject;
determining that the pre-determined numerical indication of the overall degree of medical risk of the subject differs by more than a specified threshold amount from the output, of the set of target outputs generated by the ANN, that is indicative of the overall degree of medical risk of the subject; and
responsively providing an indication via a user interface that the pre-determined numerical indication of the overall degree of medical risk of the subject differs from the output, of the set of target outputs generated by the ANN, that is indicative of the overall degree of medical risk of the subject.

13. The method of claim 1, wherein predicting at least one of (i) a degree of severity of the specified disease or syndrome or (ii) an amount of care that the subject will receive related to the specified disease or syndrome comprises predicting at least one of: a likelihood of mortality or a likelihood of inpatient hospitalization longer than two days.

14. The method of claim 1, wherein predicting at least one of (i) a degree of severity of the specified disease or syndrome or (ii) an amount of care that the subject will receive related to the specified disease or syndrome comprises applying a classifier to the set of target outputs for the target radiographic image.

15. The method of claim 14, wherein the applying the classifier to the set of target outputs for the target radiographic image comprises applying a generalized linear model to the set of target outputs for the target radiographic image.

16. The method of claim 14, wherein applying the classifier to the set of target outputs for the target radiographic image comprises determining a weighted sum of the set of target outputs for the target radiographic image and comparing the weighted sum to a pre-specified threshold value.

17. The method of claim 1, further comprising:
applying an additional ANN to the target radiographic image to generate one or more additional outputs, wherein the additional ANN has been trained based on an additional training set that includes a plurality of training examples from people determined to have the specified disease or syndrome, and wherein predicting at least one of (i) a degree of severity of the specified disease or syndrome or (ii) an amount of care that the subject will receive related to the specified disease or syndrome based on the set of target outputs for the target radiographic image comprises predicting at least one of (i) a degree of severity of the specified disease or syndrome or (ii) an amount of care that the subject will receive related to the specified disease or syndrome based on the set of target outputs for the target radiographic image and the one or more additional outputs.

18. The method of claim 17, wherein the one or more additional outputs of the additional ANN are indicative of at least one of a severity of lung opacity, a degree of lung opacity, or an extent of lung opacity depicted in the target radiographic image.

19. The method of claim 18, wherein the specified disease or syndrome is SARS-CoV-2 or a variant thereof.

20. A non-transitory computer-readable medium, having stored thereon program instructions that, upon execution by a computing device, cause the computing device to perform a method comprising:

receiving a target radiographic image of a chest of a subject, wherein the subject has a specified disease or syndrome, wherein an artificial neural network (ANN) has a set of inputs and a set of outputs, wherein the ANN has been trained by a training set including a plurality of radiographic images containing features that are mapped to the set of inputs and associated with labeled values mapped to the set of outputs, wherein a subset of the radiographic images contain instances of the features that are indicative of at least one comorbidity within a particular comorbidity class and are associated with instances of the labeled values that represent the particular comorbidity class, wherein the ANN a common layer and a plurality of parallel output heads, wherein the common layer provides outputs to the plurality of parallel output heads, and wherein each output head of the plurality of parallel output heads generates, as an output, a respective one of the set of outputs;

applying the ANN to the target radiographic image to generate a set of target outputs for the target radiographic image, wherein output values of the set of target outputs indicate that the subject has at least one comorbidity in the particular comorbidity class;

based on the set of target outputs for the target radiographic image, predicting at least one of (i) a degree of severity of the specified disease or syndrome or (ii) an amount of care that the subject will receive related to the specified disease or syndrome;

based on the set of target outputs for the target radiographic image, predicting a likelihood that the subject has a specified disease or syndrome;

determining that the likelihood that the subject has the specified disease or syndrome has an intermediate value; and responsive to determining that the likelihood that the subject has the specified disease or syndrome has an intermediate value, performing an additional diagnostic test on the subject to determine whether or to what degree the subject has the specified disease or syndrome.

* * * * *